US008828485B2

(12) United States Patent
Lian et al.

(10) Patent No.: US 8,828,485 B2
(45) Date of Patent: Sep. 9, 2014

(54) CARBON-ENCASED METAL NANOPARTICLES AND SPONGES AS WOOD/PLANT PRESERVATIVES OR STRENGTHENING FILLERS

(75) Inventors: Kun Lian, Baton Rouge, LA (US); Qinglin Wu, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 153 days.

(21) Appl. No.: 13/249,558

(22) Filed: Sep. 30, 2011

(65) Prior Publication Data

US 2012/0021222 A1    Jan. 26, 2012

Related U.S. Application Data

(62) Division of application No. 12/278,295, filed as application No. PCT/US2007/061862 on Feb. 8, 2007, now abandoned.

(60) Provisional application No. 60/772,325, filed on Feb. 10, 2006.

(51) Int. Cl.
| | |
|---|---|
| *B05D 3/12* | (2006.01) |
| *B05D 7/22* | (2006.01) |
| *B32B 5/16* | (2006.01) |
| *B01J 13/02* | (2006.01) |
| *B27K 3/00* | (2006.01) |
| *B27K 3/32* | (2006.01) |
| *A01N 59/16* | (2006.01) |
| *B27K 3/16* | (2006.01) |
| *A01N 59/20* | (2006.01) |
| *A01N 25/28* | (2006.01) |
| *A01N 25/26* | (2006.01) |
| *B27K 3/52* | (2006.01) |

(52) U.S. Cl.
CPC ......... *B01J 13/02* (2013.01); *B01D 2255/9202* (2013.01); *B27K 3/007* (2013.01); *B27K 2200/10* (2013.01); *B27K 3/32* (2013.01); *B01D 2255/1021* (2013.01); *A01N 59/16* (2013.01); *B27K 3/16* (2013.01); *A01N 59/20* (2013.01); *A01N 25/28* (2013.01); *B28Y 30/00* (2013.01); *A01N 25/26* (2013.01); *B01D 2255/1023* (2013.01); *B27K 2200/30* (2013.01); *B27K 3/52* (2013.01)
USPC ........ 427/181; 427/388.1; 427/397; 428/328; 428/403; 428/407; 428/541

(58) Field of Classification Search
CPC ............ B27K 3/00; B27K 3/005; B27K 3/22; B27K 3/16; B27K 3/52; A01N 25/26; A01N 25/28; A01N 59/16; A01N 59/20
USPC .................. 428/403–407, 328, 541; 427/181, 427/388.1, 397
See application file for complete search history.

(56) References Cited

U.S. PATENT DOCUMENTS

| | | | |
|---|---|---|---|
| 4,923,894 A * | 5/1990 | Kanda et al. ................... | 514/493 |
| 4,973,501 A | 11/1990 | Gradeff ......................... | 427/440 |

(Continued)

FOREIGN PATENT DOCUMENTS

WO   WO / 2006/065684    6/2006

OTHER PUBLICATIONS

Cioffi et al., Antifungi activity of polymer-based copper nanocomposite coatings, Applied Phys. Lett. 85, 2417 (2004); DOI: 10.1063/1.1794381.*

(Continued)

*Primary Examiner* — Holly Le
(74) *Attorney, Agent, or Firm* — John H. Runnels

(57) ABSTRACT

We disclose novel metallic nanoparticles coated with a thin protective carbon shell, and three-dimensional nano-metallic sponges; methods of preparation of the nanoparticles; and uses for these novel materials, including wood preservation, strengthening of polymer and fiber/polymer building materials, and catalysis.

19 Claims, 16 Drawing Sheets

(56) References Cited

U.S. PATENT DOCUMENTS

| | | | |
|---|---|---|---|
| 5,196,407 A * | 3/1993 | Goletz et al. | 514/63 |
| 5,547,748 A | 8/1996 | Ruoff et al. | 428/323 |
| 5,874,025 A * | 2/1999 | Heuer et al. | 252/383 |
| 6,265,333 B1 | 7/2001 | Dzenis et al. | 442/346 |
| 6,479,028 B1 | 11/2002 | Kaner et al. | 423/414 |
| 6,521,288 B2 * | 2/2003 | Laks et al. | 427/180 |
| 6,753,035 B2 | 6/2004 | Laks et al. | 427/180 |
| 6,843,837 B2 * | 1/2005 | Zhang et al. | 106/18.32 |
| 7,593,502 B2 * | 9/2009 | Katcha et al. | 378/4 |
| 2002/0132361 A1 | 9/2002 | Vossmeyer et al. | 436/151 |
| 2003/0134137 A1 | 7/2003 | Laks et al. | 428/537.1 |
| 2004/0258767 A1 * | 12/2004 | Leach et al. | 424/630 |
| 2004/0258768 A1 | 12/2004 | Richardson et al. | 424/630 |
| 2005/0092241 A1 | 5/2005 | Colibaba-Evulet | 118/715 |
| 2005/0255251 A1 | 11/2005 | Hodge et al. | 427/397 |
| 2005/0265893 A1 * | 12/2005 | Leach et al. | 422/40 |
| 2006/0112850 A1 * | 6/2006 | Zhang et al. | 106/15.05 |
| 2008/0260841 A1 * | 10/2008 | Leach et al. | 424/630 |
| 2009/0098033 A1 * | 4/2009 | Lian et al. | 423/213.5 |

OTHER PUBLICATIONS

Hata et al., "Electroc Microsopic Study on Pyrolysis of CCA (Chromium, Copper and Arsenic Oxide)-Treated Wood," J. Anal. Appl. Pyrolysis, vol. 68-/69, pp. 637, 639, and 641 (2003).

He, J. et al., "Facile in situ synthesis of noble metal nanoparticles in porous cellulose fibers," Chem. Mater., vol. 15, pp. 4401-4406 (2003).

He, J. et al., "Facile fabrication of composites of platinum nanoparticles and amorphous carbon films by catalyzed carbonization of cellulose fibers," Chem. Commun., Issue 4, pp. 410-411 (2004).

Raymond et al, "In-Situ Synthesis of Ferrites in Cellulosics," Chem. Mater. 6:249-255 (1994).

Zhu, H. et al., "Synthesis of assembled copper nanoparticles from copper-chelating glycolipid nanotubes," Chem. Phys. Lett., vol. 405, pp. 49-52 (2005).

* cited by examiner

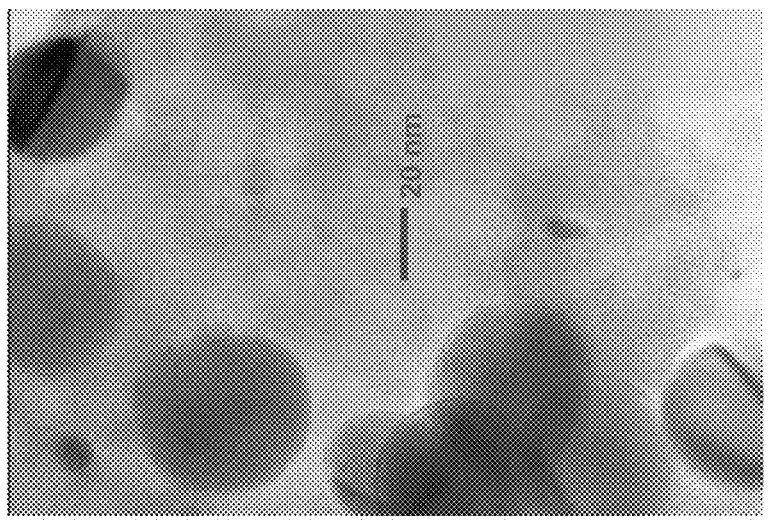
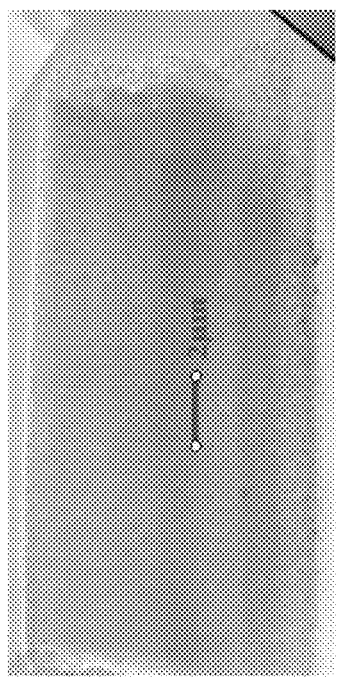
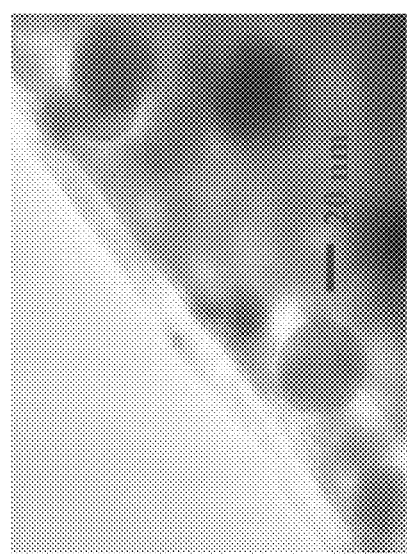
Fig. 2C
Fig. 2A
Fig. 2B

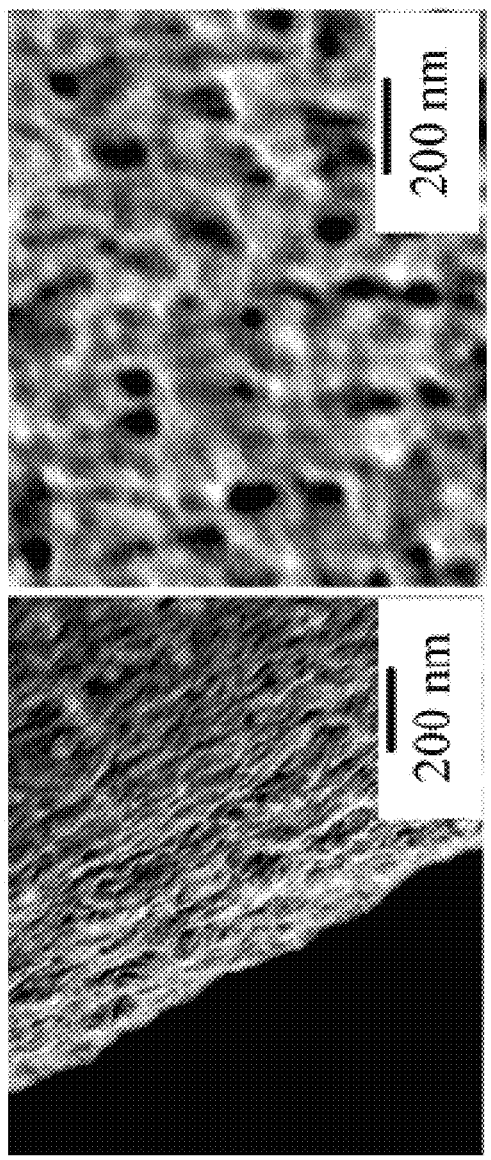

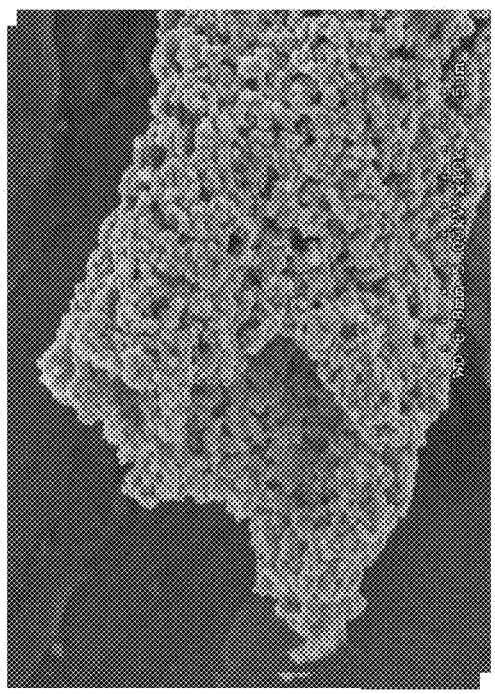
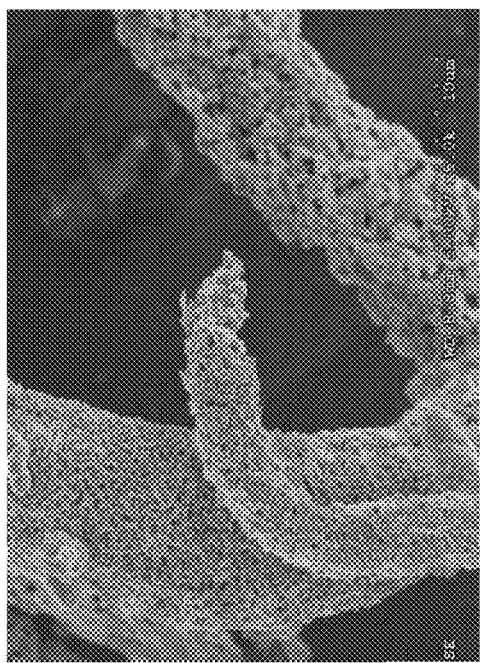
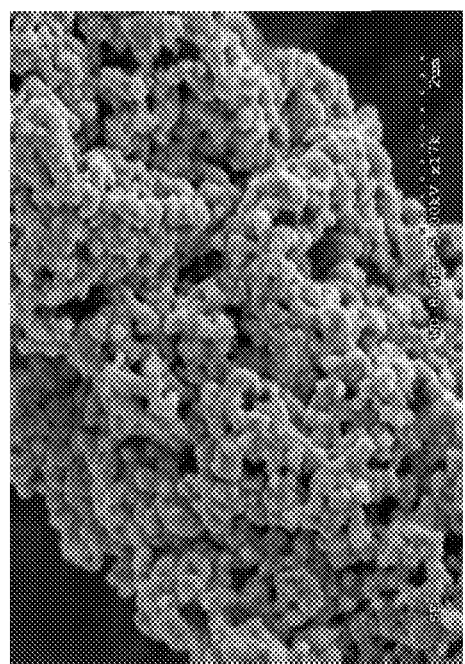
Fig. 7A
Fig. 7B
Fig. 7C

CARBON-ENCASED METAL NANOPARTICLES AND SPONGES AS WOOD/PLANT PRESERVATIVES OR STRENGTHENING FILLERS

This application is a divisional of application Ser. No. 12/278,295, filed Aug. 5, 2008; which is the national stage of international application PCT/US2007/061862, international filing date Feb. 8, 2007; which claimed the benefit of the Feb. 10, 2006 filing date of provisional application Ser. No. 60/772,325 under 35 U.S.C. §119(e). The complete disclosures of each of these priority applications are hereby incorporated by reference in their entirety.

TECHNICAL FIELD

This invention pertains to metal-core carbon-shell nanoparticles ("MCCSNPs") and nano-metallic Sponges, methods of making MCCSNPs and nano-metallic sponges, and methods for using MCCSNPs, for example, in the protection of wood and in the strengthening of polymers and composites.

BACKGROUND ART

Metallic Nanoparticles and Methods for Generating

Nanomaterials offer unique properties (e.g., magnetic, optical, mechanical, and electronic) that vary with changes in particle size. Metal-based nanoparticles such as Au, Pt, Cu, and Ag, and metallic oxides, for example, $Fe_xO_y$, have been used as industrial chemicals, catalysts, optical media, magnetic storage materials, materials for enhancing magnetic resonance imaging (MRI), and electrode materials.

However, metallic nanoparticles without a protective coating often have a high propensity to oxidize or undergo other chemical reactions. Metal-core carbon-shell nanoparticles (sometimes referred to as "carbon-encased metal nanoparticles"), which have a metallic core surrounded by a carbon shell, can broaden the uses of metallic nanoparticles. The metal in such nanoparticles is protected against chemical reactions, and the carbon shells may be functionalized to have specific physical, chemical, and biological properties.

Currently, synthesis of metal-core carbon-shell nanoparticles is based on wet chemical or expensive physical methods that would be difficult to scale for commercial applications. The common techniques to make these and other types of nanoparticles are described below.

Metal Evaporation is a simple way to fabricate metal/metal oxide nanoparticles. A mixture of a metal and its oxide is placed in a basket or pouch through which an electrical current is passed. This process causes the metal and its oxide first to melt and then to vaporize. An electron beam may be used to assist in vaporizing metal/metal-oxide mixtures having high melting temperatures. Vaporization may occur either in vacuum or in an inert gas. Vaporized metal/metal-oxides are solidified directly on a substrate placed above the basket or pouch. The size and size distribution of such particles depend on a number of parameters including whether they are generated in an inert gas or vacuum, and if in a vacuum, the pressure. Metallic nanoparticles produced by this method tend to be very reactive, which is useful for some applications but undesirable for others.

Sonochemical processing is a method for generating nanoparticles in an ultrasonicated solvent. Sonochemistry involves acoustic cavitation, which appears to be caused by an implosive collapse of a bubble in an ultrasonically irradiated liquid. This process generates a transient, localized hot spot with an effective temperature of about 5000° K at pressures of about 1000 atm. Heating and cooling rates may be greater than 1000° K/s. Acoustically cavitated bubbles produce large pressure variations and fluid motion. In addition, there may be other sonochemical effects, such as momentum and mass transport, generation of radicals and other excited particles, formation of high velocity liquid jets, and generation of shockwaves external to the bubble. While metallic nanoparticles may be made by this method, the process is difficult to control.

Chemical Reduction of metal ions in solution may be used to form metallic nanoparticles. This process begins with a solution of a metal ion. A reducing agent added to the solution causes precipitation of the metal, metal alloys, or metal carbides. Poly-alcohols, such as ethylene glycol or diethylene glycol, have been used as both solvent and reductant. Particle size of precipitants depends on the rate of nucleation and growth, and may be affected by aggregation during growth. This method has been used to form Au, Cu, Te, and Pt nanocrystalline metals, and nanocrystalline intermetallics.

Protective Layers. Because of their high surface area-to-volume ratio, many metallic nanoparticles, including copper nanoparticles, are prone to readily oxidize or otherwise chemically react. To avoid this problem a protective layer may be formed around the nanoparticles. Several techniques, such as layer-by-layer assembly, formation of microemulsion, modifications of the Kratschmer-Huffman carbon arc method, hydrocarbon decomposition, arc discharge in de-ionized water, hydrolysis of tetraethoxysilicate (TEOS), plasma polymerization, plasma torch synthesis, and flow-levitation have been used to coat metallic nanoparticles. Some of the more common methods are described below.

Layer-by-Layer Assembly (LBL) is a method for fabrication of composite nanomaterial films. This method is based on the sequential adsorption of substrates in solutions of oppositely charged compounds. Nanometer film thicknesses are typical. Deposition is controlled by adjusting processing conditions, such as solution pH, ionic strength, and immersion time.

Microemulsion is a method in which two or more immiscible substances are dispersed. This dispersion or mixture typically contains water, oil, a surfactant, and sometimes a co-surfactant. An oil-in-water (O/W) microemulsion is one in which oil is at a droplet center surrounded by surfactant and co-surfactant. A water-in-oil (W/O) microemulsion is one in which water is at a droplet center surrounded by oil. The submicroscopic droplets/micelles may take up solutes and often exhibit different environments than exhibited by bulk solvents. Microemulsion droplets have been used to encapsulate water-soluble agents such as nanoparticles and submicron particles.

Kratschmer-Huffman Carbon Arc is a method originally used to make fullerenes. The method uses graphite rod electrodes to produce a continuous DC electric arc discharge in vacuum. Carbon that evaporates from an anode produces carbon soot. In high vacuum, the method produces a hard, graphite-like substance, while at lower vacuum it forms a fine soot rich in fullerenes and other nano-materials. This method has been modified by simultaneously evaporating carbon and a metal to generate nanoparticles comprising a carbonaceous material that encapsulates a metal nanoparticle. However, it appears that this process often results in the metal being oxidized.

Typically the existing methods for generating core-shell or coated metal nanoparticles are either too selective or too difficult to implement. For example, the LBL method has been reported to date to be limited to polymer and coated noble metal nanoparticles.

The microemulsion method cannot be applied generally because it requires very specific recipes for each metal salt. Further this method is limited by the reducing potential of the metal salt. In addition, nanoparticles generated by the microemulsion method tend to agglomerate. Further, like the LBL method, this method has been reported to date only to produce polymer or coated noble metal nanoparticles.

While the Kratschmer-Huffman carbon arc method appears to produce high quality carbon shells on metal particle surfaces, it also produces numerous by-products, nanoparticles with large variations in shape and size, and some metal oxides.

In addition, none of the existing methods for generating metallic nanoparticles routinely achieve complete carbon coating which provide complete protection of metallic nanoparticles. The metallic nanoparticles tend to oxidize readily in air from the exposed surfaces, resulting in a short shelf-life for these materials unless stored under an inert gas. Scaled-up production using any of these methods also will be difficult and expensive, because precise control of the method variables is difficult.

J. He et al., "Facile synthesis of noble metal nanoparticles in porous cellulose fibers," *Chem. Mater.*, vol. 15, pp. 4401-4406 (2003) reported in situ, wet-chemistry formation of Ag, Au, Pt, or Pd nanoparticles in porous cellulose fibers from the corresponding noble metal salt precursors, using a traditional reducing agent ($NaBH_4$). This method was not reported to produce a carbon shell.

J. He et al., "Facile fabrication of composites of platinum nanoparticles and amorphous carbon films by catalyzed carbonization of cellulose fibers," *Chem. Commun.*, Issue 4, pp. 410-411 (2004) reported carbonizing cellulose matrixes containing reduced platinum nanoparticles. J. He et al proposed that the platinum nanoparticles may have catalyzed the carbonization of the cellulose matrix. The resulting product consisted primarily of amorphous carbon fibers and Pt nanoparticles.

H. Zhu et al., "Synthesis of assembled copper nanoparticles from copper-chelating glycolipid nanotubes," *Chem. Phys. Lett.*, vol. 405, pp. 49-52 (2005) reported an annealing process for assembling copper nanoparticles from copper-chelating amphiphiles using glycolipid nanotubes.

Raymond et al, "In-Situ Synthesis of Ferrites in Cellulosics," *Chem. Mater.* 6:249-255 (1994) disclosed that nanoferrite particles could be generated within a cellulosic matrix. This method appears to use an ion-exchange mechanism to retain these particles within the cellulosic matrix. No carbonization of this material was reported.

There exists an unfilled need for metallic nanoparticles that are stable in air and water, while still exhibiting desirable chemical activity, and a method of generating such metallic nanoparticles that is cost efficient and scalable for industrial use.

Wood Preservation

Millions of homes are constructed each year from light frames made of wood. Wood, unless protected, is naturally degraded by heat, moisture, insects, decay, mold and other forces. Formosan subterranean termites (*Coptotermes formosanus*) can be particularly destructive to wood.

It is well known that copper is a very effective wood preservative. In recent years, primarily because of environmental concerns, the most widely used form of copper, chromated copper arsenate ("CCA"), has been substantially reduced. Removal of CCA from the market has made wood preservation more difficult.

Laks et al, U.S. Pat. No. 6,753,035 disclosed a method for incorporating additives such as biocides into wood or wood products using polymeric nanoparticles.

Richardson et al, PCT Application WO 2006/065684 disclosed methods for protecting wood against insect attack and decay by injecting sparingly soluble copper hydroxide-containing particles into wood and wood products. This disclosure taught the use of micron size particles, and suggested that particles smaller than 0.02 microns would tend to convert from metallic copper to copper oxide and be easily flushed from the wood.

Copper-containing wood preservatives that have been proposed to replace CCA typically use one or more soluble copper ions (e.g., $Cu^{++}$). Copper complexes such as copper alkanolamine complexes, copper polyaspartic acid complexes, alkaline copper quaternary salts, ammoniacal copper quaternary salts, ammoniacal copper zinc salts, copper azole, copper boron azole, copper bis-(dimethyldithiocarbamate), ammoniacal copper citrate, copper citrate, and copper alkanolamine carbonate complexes have been suggested. However, due primarily to cost, the only formulations that have been used commercially are copper alkanolamine complexes and copper ammonium complexes.

Wood is naturally resistant to mildews and certain molds, in part because there is very little fixed nitrogen in wood. However, amine and ammonium complexes that add nitrogen to the wood may paradoxically promote mildew or mold. For example, amine and ammonium copper complexes appear to facilitate increased sapstain mold formation and enhanced mildew formation.

Another problem with commercially available copper-based preservatives is that they tend to be water-soluble, making them subject to leaching from wood exposed to moisture. To maintain protective amounts of copper in wood, a higher concentration of copper may need to be impregnated into the wood. While such an approach does not prevent leaching, it does increase the time during which the copper is effective. However, since the copper ions are thought to be toxic to aquatic life, such an increase in the copper loading is not desirable because of the associated increase in copper ions discharged into the environment. In addition, increasing the amount of copper increases the cost of this process. Also, because amine and ammonium complexes may emit vapors, large amounts of these complexes of copper tend to increase the odor and irritation from the amine and ammonia fumes.

Another problem with existing commercial, copper-containing wood preservatives is that they often cause corrosion of metal fasteners and other hardware. Metal ions as well as amines, alkanolamines, and ammonia used in soluble copper treatments appear to contribute to corrosion of metal hardware. Thus, commercial copper-based wood preservative may not be suitable for outdoor wooden structures, unless galvanized metal or stainless steel is used for all fittings. Use of such hardware will make the wooden structure more costly.

An unfilled need exists for copper-containing wood preservatives that are economical, that do not readily leach, that do not emit noxious vapors, and that do not cause corrosion of fasteners.

Strengthening Polymer and Polymer Composite Materials

Polymers offer many advantages over conventional building materials including lightness, resistance to corrosion and ease of processing. Polymers may be used alone or in combination with fibrous materials. In addition, polymers may be used as additives to form composites, which may be used as structural members. Polymer composites can be used in many different forms ranging from structural composites in the construction industry to the high technology composites of the aerospace and space satellite industries.

In recent years, composites comprising natural fibers, for example wood, and reinforced plastic have become one of the most rapidly growing markets within the polymer industry. In some markets more than 80% of products such as decking, railing, windows, door profiles, and shingles are either polymeric or fiber/polymer composites. Other uses of these materials include infrastructure, for example boardwalks, docks, and related structures, in the transportation industry, in automobiles, for example interior panels, rear shelves, and spare tire covers, and within the industrial/consumer industry, for example picnic tables, park benches, pallets, and other similar products.

However, some concerns over product quality and product toughness remain. Using wood or other natural fiber as filler in composites increases composite stiffness, but appears to reduce the toughness of the composite. Brittleness appears to be caused in part by stress concentrations at fiber ends and by poor interfacial adhesion.

Thus an unfilled need exists for new additive or coupling agents for composites that improve toughness while maintaining or improving other composite properties.

SUMMARY OF THE INVENTION

Novel Material

Metal-Core Carbon-Shell Nanoparticles

We have discovered nano-metallic materials coated with a thin carbon layer. Prototypes have been made with metallic particle sizes less than 10 μm, and preferably less than 50 nm, and more preferably less than 10 nm, wherein the metal typically exists in a zero oxidation state. In one embodiment, nano-size metal particles are completely coated with a protective carbon shell, wherein said carbon shell has a thickness of less than 20 nm, and preferably less than 10 nm, and more preferably less than 1 nm, and more preferably less than 0.5 nm. Further said particles, when completely coated with carbon shells, are stable against oxidation. In the special case of carbon-encased noble metals, the metal core is resistant to attack by reagents that will otherwise dissolve or react with such metals, for example aqua regia.

We have also discovered a novel process for making these nano-metallic, carbon-coated particles. This process comprises loading metal ions into fibers of biological origin, and then carbonizing the fibers. While not wishing to be bound by this theory, it appears that the metal ions are reduced into metal nanoparticle cores at natural interstices or other nanostructures in the natural fibers. The metals are reduced into nanoparticle cores, and carbon shells are formed around the cores, more-or-less simultaneously when the metal-ion impregnated natural fibers are heated. In one embodiment, the carbonizing temperature is sufficient to form a thin carbon shell encasing a metal nanoparticle. The carbonization temperature will differ for different metals and for different fibers.

Natural biological systems often exhibit highly controlled and organized structures. The unique microstructures found in natural biological system may provide templates for producing metallic nanomaterials within a carbon shell. The process of making nanoparticles and nanoscale materials using biological molecules through physical and chemical methods has been reported in the past. However, synthesizing nano-structures and materials, especially the core-shell structure nanoparticles, using natural fiber bio-templates from a carbonization process has never been previously reported Depending on the respective oxidation potentials and kinetics, the formation of core/shell nanoparticles for some metals may benefit by the presence of an additional reducing agent in the reaction, e.g., hydrogen gas, methane, thiosulfate, ferrous ion, borohydride, oxalic acid, or stannous ion. An additional reducing agent, aside from the natural fiber itself, was not found to be necessary for prototype demonstrations with copper, silver, nickel, and gadolinium.

The invention may be practiced with naturally-occurring plant fibers or animal fibers that have micro-pore structures. Plant fibers are based on cellulose, with or without the presence of lignin or hemilignin. Representative plant fibers include cotton, flax, linen, jute, ramie, sisal, hemp, milkweed, straw, bagasse, hardwoods, and softwoods. Animal fibers are largely based on proteins, for example, silk, hair, wool, spider silk, silkworm silk, sinew, and catgut.

Ions of metals, in addition to Cu, Ag, Ni, and Gd, may also be used. For example, the invention may be practiced with Group IIA metals (Be, Mg, Ca, Sr, Ba, Ra); Group IIIA metals or semi-metals (B, Al, Ga, In, Tl); Group IVA metals or semimetals (Si, Ge, Sn, Pb); Group VA metals or semi-metals (As, Sb, Bi); Group VIA semi-metals (Te, Po); Group IIIB metals (Sc, Y, La, Ac); Group IVB metals (Ti, Zr, Hf): Group VB metals (V, Nb, Ta); Group VIB metals (Cr, Mo, W); Group VIIB metals (Mn, Tc, Re); Group VIII metals (Fe, Co, Ni, Ru, Rh, Pd, Os, Ir, Pt); Group IB metals (Cu, Ag, Au); Group IIB metals (Zn, Cd, Hg); Lanthanides (Ce, Pr, Nd, Pm, Sm, Eu, Gd, Tb, Dy, Ho, Er, Tm, Yb, Lu); and Actinides (Th, Pa, U, Np, Pu, Am). Further, mixtures of metals may be used.

Without wishing to be bound by this hypothesis, it is believed that the three-dimensional structure of the native fiber provides a framework or template for seeding the nascent nanoparticles, as well as providing the carbon that will form the shell. Semi-synthetic derivatives of native fibers can in some cases sufficiently preserve the framework, the template, and accordingly may be used in this invention. For example, rayon, which is derived from cellulose, has been successfully used in preparing copper/carbon core/shell nanoparticles in accordance with this invention. By contrast, totally synthetic fibers (e.g., nylon) have not, to date, been successful when used in an otherwise similar process. Without wishing to be bound by this theory, we believe that this may be because totally synthetic fibers generally lack the complex three-dimensional framework or template that is characteristic of native fibers, and that provide seeding loci for the formation of metallic nanoparticles.

Aqueous, non-aqueous, or mixed solvents may be used in practicing the invention. The principal requirement of the solvent is that it should dissolve the metal ion being used. In general, distilled water is a preferred solvent, but other solvents may also be used. Examples of such solvents include methanol, ethanol, other alcohols, DMSO, DMF, hexamethylphosphorotriamide, formic acid, acetic acid, formic acid, acetone, and acetonitrile.

The novel core/shell nanoparticles were dispersible in both water and organic solvents (such as oil). They were produced at a very low cost, and the encased metal was stable in air or water for months, without oxidation or other chemical reaction.

In one prototype embodiment, $Cu^{+2}$ ions were impregnated into cotton fiber (which contains naturally occurring cellulose, $(C_6H_{10}O_5)_n$); extra solvent was removed from the impregnated fiber and then carbonized at about 350° C. for about 2 hours. The resulting material contained copper-core-carbon-shell nanoparticles (CCCSNPs).

Nano-Metallic Sponges

Alternatively the present invention may be used to make three-dimensional nano-metallic sponges. The process is generally similar to that for making the core/carbon shell nanoparticles, but the metal ion-impregnated natural fibers are heated to a higher temperature, to a point where carbon is vaporized, and the metal nanoparticles just start to sinter and connect to one another to form nano-sponge structures. The fiber skeleton acts as a frame/template to make tube-like nano-sponges, which have a far greater active surface area/volume ratio than most prior high surface area metallic structures. Previous catalyst structures using nanoparticles have generally supported those nanoparticles on a matrix to enhance surface area/volume. But the prior structures are mainly two-dimensional because the nanoparticles rest on a generally inactive matrix material that blocks some of the nanoparticle surface. Many commercial catalysts are shipped with protective compounds, and are activated on-site before use. For nano-sponge structures made in accordance with the present invention, after sintering without exposure to air, the sponge is nearly pure metal. Upon exposure to air, a metal oxide may be formed.

For example, prototype nano-metallic sponges have been made by soaking natural fibers in a metal ion solution as previously described, followed by carbonizing the impregnated fibers at elevated temperature in an inert atmosphere (or under vacuum). A somewhat higher temperature is used to form nano-metallic sponges than the core/shell nanoparticles. For example, we have found that for copper a preferred temperature for forming core/shell nanoparticles is about 350° C., and a preferred temperature for forming nano-metallic sponges is about 450° C. For silver, the corresponding temperatures are about 180° C. and about 280° C., respectively.

Without wishing to be bound by this hypothesis, it is believed that core-shell nanoparticles are formed throughout the entire carbonized fiber skeleton first, as an intermediate step in the formation of nano-metallic sponges. The carbonized fiber skeleton structure acts as a template for the formation of the sponge, meaning that the carbonized fiber skeleton is preferably not pulverized into a fine powder before sintering. The nano-metallic sponge forms on and around the carbonized fiber skeleton, leading to a hollow tube structure with a very high surface area-to-volume ratio during the late sintering process. Nano-metallic sponges may be formed in a single, continuous process, comprising heating the fiber to form nanoparticles embedded in the carbonized fiber skeleton, and then raising the temperature until nano-metallic sponges are formed. In another alternative, the nano-metallic sponges (or the core-shell nanoparticles, for that matter) may be formed in situ with the ion-impregnated fibers. Or the nano-metallic sponges may be formed in two steps: First, the nanoparticles are formed, embedded in the carbonized fiber skeleton, in one location. Second, the carbonized skeleton with nanoparticles is positioned in a designated place and heated to form a sponge with a fresh surface in situ, in a second location, where the sponge is to be used (typically, as a catalyst). This last approach may be particularly attractive for industrial applications. Because metal catalysts can often be sensitive to ambient conditions, it can be useful to prepare a catalyst with a fresh surface directly inside a reactor only when needed.

At this higher temperature metal nanoparticles sintered and interconnected, forming nano-sponge structures. The fiber skeleton provided a frame/template to generate tube-like nano-sponges as shown in FIGS. 7A-7C and FIGS. 8A-8B. FIGS. 7A-7C depict Cu/C nano-metallic sponges, and FIGS. 8A-8B depict Ag/C nano-metallic sponges. The nano-metallic sponges exhibited large surface areas. The resulting nanoparticle structures may be used either without support or with another support structure. Further nano-metallic sponges may comprise a mixture of one or more metals. Nano-metallic sponges made in accordance with the present invention are expected to exhibit a high number of active catalytic sites per unit volume.

Uses for the Novel Materials

Copper nanoparticles, for example, have many industrial applications due to their unique physical, optical, and chemical properties, but they are generally extremely sensitive to their environment. Coating copper nanoparticles with a carbon layer appears to protect the copper against oxidation, while allowing the particles to retain useful properties. Other encapsulated metals, such as Ni, Zn, Fe, Cr, Pt, Pd, W, Re, and mixtures of metals, may be used in applications, such as catalysis and protection of wood and live plants. In addition, the carbon shells also provide surfaces for chemical functionalization or surface modification. Surface modifications may be used in applications such as biological and biomedical diagnoses, catalysis, fuel cells, drug delivery, paint and coating technology, sonar, and magnetic particle technology.

Wood Preservative

Copper-based reagents are known to be effective wood preservatives, but as noted above, current formulations tend to leach from wood in the presence of moisture, they tend to corrode metal fasteners, and they may cause wooden structures to emit offending vapors. While low oxidation state copper nanoparticles otherwise rapidly oxidize in air, by coating the surface of copper nanoparticles with a thin carbon layer we were able to protect $Cu^o$ against oxidation. However, even though the copper was coated, it retained its wood preservation properties. Our novel form of copper, CCCSNPs, was effective for wood preservation, protecting for example against Formosan termites and decay, while it persisted in wood in the presence of moisture. This novel material did not cause corrosion of metal hardware, nor did it give off offensive vapors. CCCSNPs appeared to be environmentally friendly wood preservatives, since copper ions were not readily leached, nor readily discharged into the environment.

The novel nanoparticles may be used in various wooden structures, including lumber, structural wood composites or lumber composites, laminated veneer lumber, parallel strand lumber, laminated strand lumber, non-structural wood composites, particleboard, hardboard, medium density fiberboard, and wood fiber-cement composites. CCCSNPs also may be incorporated into a composite either while being made or after being formed, and they may be inserted into wood using standard pressurization techniques, or they may be taken up directly by living plants.

Catalysis

Cellulose is a natural carbohydrate (polysaccharide) containing anhydroglucose units joined by an ether linkage to form a linear molecular chain. Natural cellulose fibers have a porous structure, with interconnecting microfibrils 10-30 nm in width. Specific surface areas are usually in the range of 30-55 $m^2$/g. FIGS. 3A and 3B are micrographs of cellulose. FIG. 3A depicts the surface of cellulose; and FIG. 3B depicts the pores. Wood has complex pore morphology within its cellulose fibers. We have used this morphology for synthesizing nanoparticles, enhancing the access of reactant molecules to catalytic centers.

In one embodiment, catalysts may be made from nano-metallic sponges. Nano-metallic sponge structures, made in accordance with the present invention without exposure to air, were nearly completely active metal. Upon exposure to air, metal oxides were formed. When a metallic-sponge is made from catalytically active metals it should either be reduced in situ or kept under a non-oxidizing atmosphere before use as a catalyst. Mixtures of metals in nano-metallic sponges may also be made.

Strengthening Polymer and Polymer Composite Materials

MCCSNPs may be used to strengthen polymeric systems, including, for example polyethylene terephthalate (PET), high density polyethylene (HDPE), polyvinyl chloride (PVC), low density polyethylene (LDPE), polypropylene (PP), polystyrene (PS), other polymers (e.g., SAN, ABS, PC, and nylon), their combinations (e.g., PET/HDPE systems), and fiber reinforced composites from various polymers.

CCCSNPs were used as impact modifier/coupling agent for HDPE and HDPE-natural fiber composites through a melt-blending process. The results showed improved impact strength. It is expected that other metal-core carbon-shell nanoparticles will also be useful for this purpose.

BRIEF DESCRIPTION OF THE DRAWINGS

FIG. 2A depicts a TEM image of Cu nanoparticles in carbonized rayon.

FIG. 2B depicts a TEM image of Cu nanoparticles as depicted in FIG. 2A in carbonized rayon at higher magnification.

FIG. 2C depicts a TEM image of Cu nanoparticles as depicted in FIG. 2B in carbonized rayon at higher magnification.

FIG. 3A depicts a micrograph of the surface of cellulose.

FIG. 3B depicts a micrograph of the pores in cellulose.

FIG. 7A depicts an SEM image of a Cu-Sponge.

FIG. 7B depicts an SEM image of a Cu-Sponge at higher magnification.

FIG. 7C depicts an SEM image of a Cu Sponge at higher magnification.

MODES FOR CARRYING OUT THE INVENTION

The general method for producing novel metal-core carbon-shell nanoparticles comprises soaking a natural fibrous material with a solution containing metal ions, removing the solvent, and then carbonizing the impregnated fibers at a temperature sufficient to generate metallic cores encased in carbon shells.

In a prototype example, we used cotton fiber as template, which was soaked in a copper sulfate solution and then extra solvent was removed. Next, we carbonized the copper-impregnated cotton fiber by heating it to between about 200° C. and about 400° C., with a preferred temperature of about 350° C. Carbonization may be carried out between a few seconds and about 3 hours, with a preferred carbonization time of about 2 hours. Carbonization may be carried out in an inert atmosphere, for example under nitrogen, or in vacuum. Carbonization may also be conducted in other non-oxidizing gases such as He, Ne, Ar, Kr, or Xe. In addition, carbonization may be carried out in reducing atmospheres, for example $H_2$, $CH_4$, etc. While not preferred, carbonization also may be carried out in an atmosphere that contains limited amounts of oxygens or other oxidizing agents, if the amounts do not adversely affect the results. While not wishing to be bound by this theory, it appears that carbonization can transform oxygen into CO, which is reducing, or into $CO_2$, which is non-oxidizing. The preferred atmosphere for carbonization is under nitrogen. The time and temperature for carbonization depend on metal ions and fibers used.

Figure 1A:
FIG. 1A depicts an SEM image of a carbonized cotton fiber impregnated with Cu.
Figure 1B:
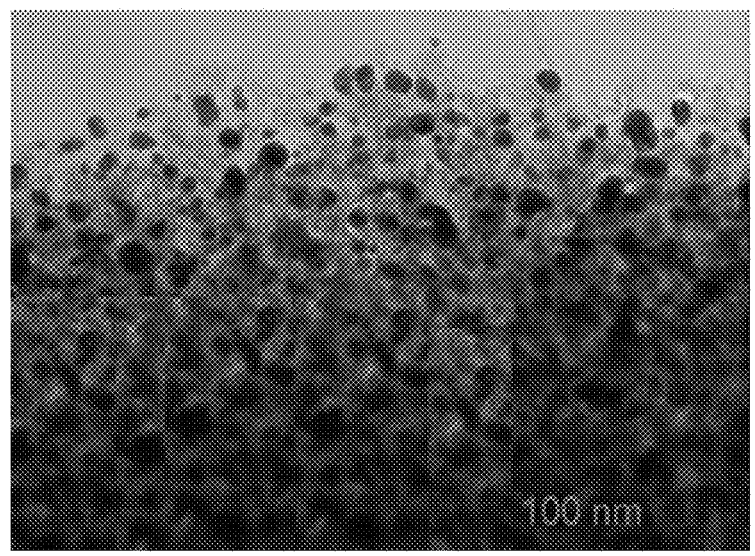
FIG. 1B depicts a TEM image of Cu nanoparticles in the carbonized cotton fiber.
Figure 1C:
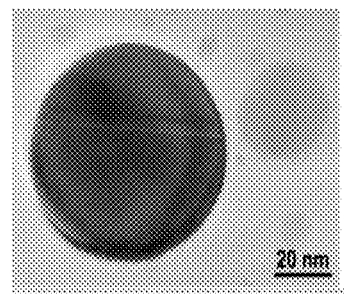
FIG. 1C depicts a TEM image of a single Cu-core Carbon-shell nanoparticle.
Figure 1D:
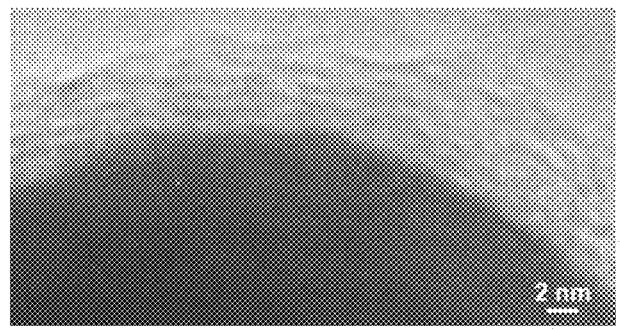
FIG. 1D depicts a nanoparticle as depicted in FIG. 1C at higher magnification.
Figure 1E:
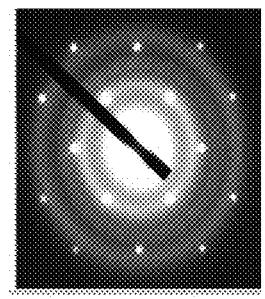
FIG. 1E depicts an electron defraction pattern of a Cu-core carbon-shell nanoparticle.
Figure 1F:
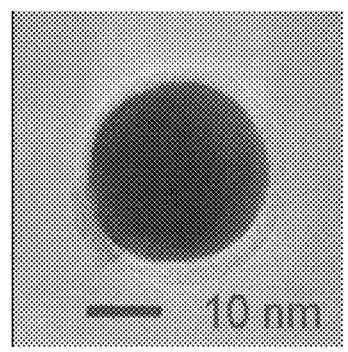
FIG. 1F depicts a higher magnification of a carbonized cotton fiber impregnated with Cu.

Copper-core carbon-shell nanoparticles ("CCCSNs") were formed during the carbonization processes without requiring further treatment. CCCSNPs appeared to be uniformly distributed throughout the carbon matrix generated during the carbonization. FIGS. 1A, 1B, 1C, 1D and 1F depict electron micrographs of fabricated copper-core carbon-shell nanoparticles made through the present invention. FIG. 1E depicts an x-ray diffraction pattern of a copper-core carbon-shell nanoparticle. FIG. 1A depicts an SEM image that shows the carbonized cotton fiber (carbon black) with many nanoparticles on its surface; FIG. 1B depicts a TEM image demonstrating that the nanoparticles were distributed throughout the carbonized cotton fiber. FIG. 1C depicts a copper core with a carbon shell surrounding it. As can be seen from FIGS. 1C and 1D, the copper core appeared to be about 50-60 nm in diameter, and the carbon shell appeared to be about 5 nm thick, respectively. FIG. 1C depicts a nanoparticle as depicted in FIG. 1D at lower magnification. FIG. 1E depicts electron diffraction pattern of Cu-core carbon-shell nanoparticle as depicted in FIG. 1C. This electron diffraction pattern indicated that the copper is in a $Cu^o$ metallic state. FIG. 1F depicts a higher magnification of carbonized cotton fiber as depicted in FIG. 1B.

Figure 4A:
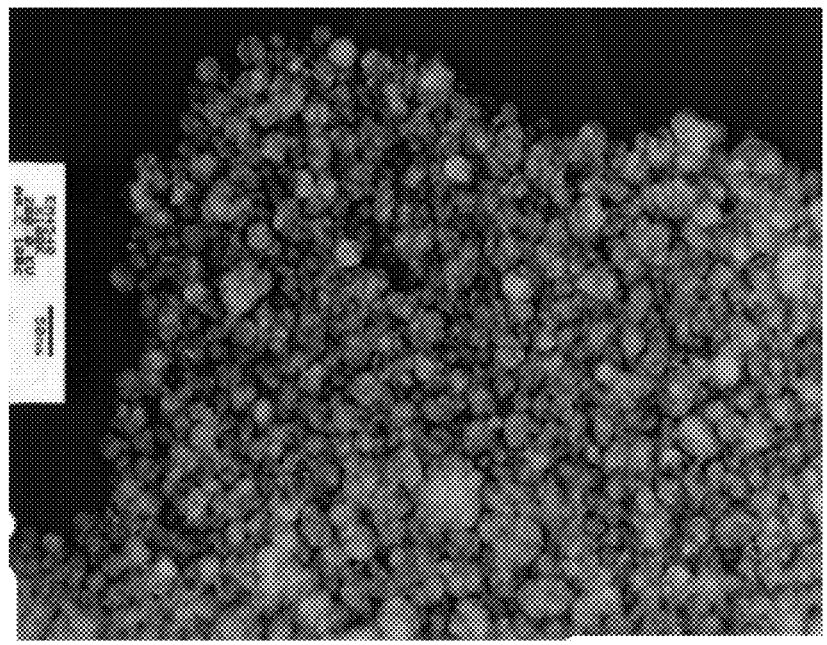
FIG. 4A depicts a TEM image of Ag nanoparticles in carbonized cotton fiber.
Figure 4B:
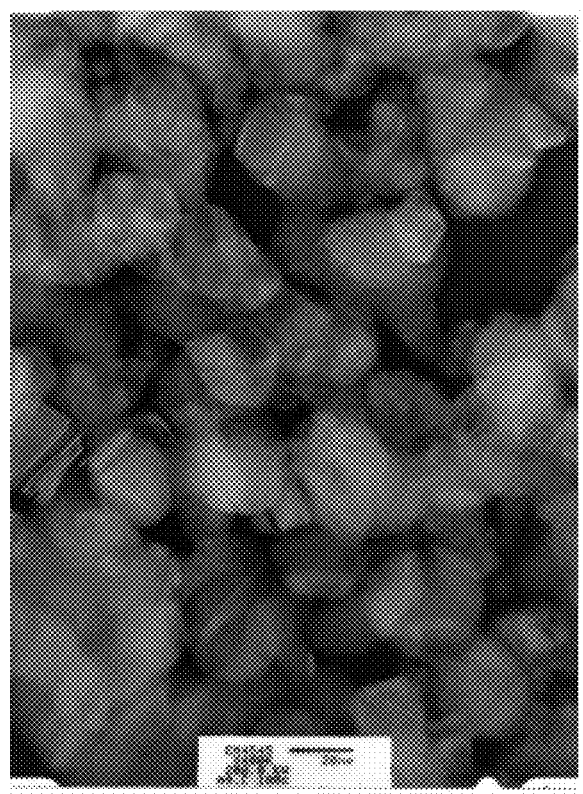
FIG. 4B depicts a TEM image of Ag nanoparticles in carbonized cotton fiber at higher magnification.
Figure 6:
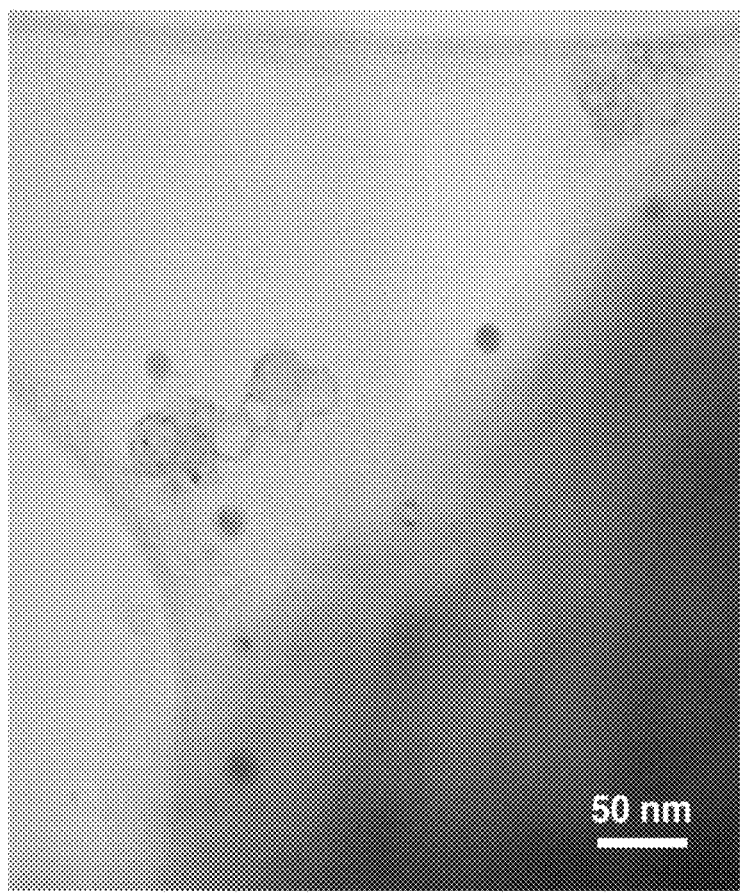
FIG. 6 depicts a TEM image of Gd nanoparticles in carbonized cotton fiber.

This invention may be carried out using almost any metal that forms soluble ions in either aqueous or non-aqueous solvents, except that group IA metals (Li, Na, K, Rb, and Cs) may be too electropositive. Silver-core carbon-shell nanoparticles, nickel-core carbon-shell nanoparticles, and gadolinium-core carbon-shell nanoparticles have all been successfully made. FIGS. 4A and 4B show electron micrographs of Ag-core carbon-shell nanoparticles at different magnifications. FIG. 6 shows an SEM micrograph of the Gd core/shell prototype.

Nickel-core carbon-shell nanoparticles were generated using the same method as described above for copper, using $NiSO_4$ as the source of Ni, except the carbonization temperature was 380° C.

Silver-core carbon-shell nanoparticles were generated using the same method as described above for copper, except silver nitrate was used as the source of silver, and the carbonization temperature was 180° C.

Galladium-core carbon-shell nanoparticles were made using the same method as described for the Cu version except $GdCl_3$ was used as the Gd source, and the carbonization temperature was 350° C.

While not wishing to be bound by this theory, it appears that the carbonization temperature correlated roughly with the melting point of the metal.

Cu-core carbon-shell materials have been successfully used to protect wood against decay.

Gd-core carbon-shell materials may be used, for example, in NMR image enhancement, energy-efficient magnetic refrigeration, and data storage. Other lanthanum-group metals, including Ce, Pr, Nd, Pm, Sm, Eu, Tb, Dy, Ho, Er, Tm, Yb, and Lu also may be used to form MCCSN materials, and these materials also should be useful for similar purposes.

Alternatively, the present invention may be used to make three-dimensional nano-metallic sponges. The process is generally similar to that for making the core/carbon shell nanoparticles, but the metal ion-impregnated natural fibers are heated to a higher temperature, to a point where carbon is vaporized, and the metal nanoparticles just start to sinter and connect to one another to form nano-sponge structures. The fiber skeleton acts as a frame/template to make tube-like nano-sponges, which have a far greater surface area/volume ratio than most prior nanoparticle structures. We have made three-dimensional nano-metallic structures, which exhibited high surface area, and which typically had particle sizes less than 10 µm, and preferably less than 50 nm, and more preferably less than 10 nm, as estimated from SEM micrographs. The metal typically existed in a low oxidation state, and in a preferred embodiment, the metal was in a zero oxidation state. Pore sizes of the metallic sponges were typically less than 100 µm, and preferably less than 100 nm, and more preferably less than 10 nm, as estimated from SEM micrographs. The sponges may exist without a carbon coating. The sponges may comprise a mixture of metals.

Prototype nano-metallic sponges have been made by soaking natural fibers in a metal ion solution as previously described, followed by carbonizing the impregnated fibers at elevated temperature in an inert atmosphere (or under vacuum). A somewhat higher temperature is used to form nano-metallic sponges than the core/shell nanoparticles. We have found that for copper a preferred temperature for forming core/shell nanoparticles is about 350° C., and a preferred temperature for forming nano-metallic sponges is about 450° C. For silver, the corresponding temperatures are about 180° C. and about 280° C., respectively.

Figure 8A:
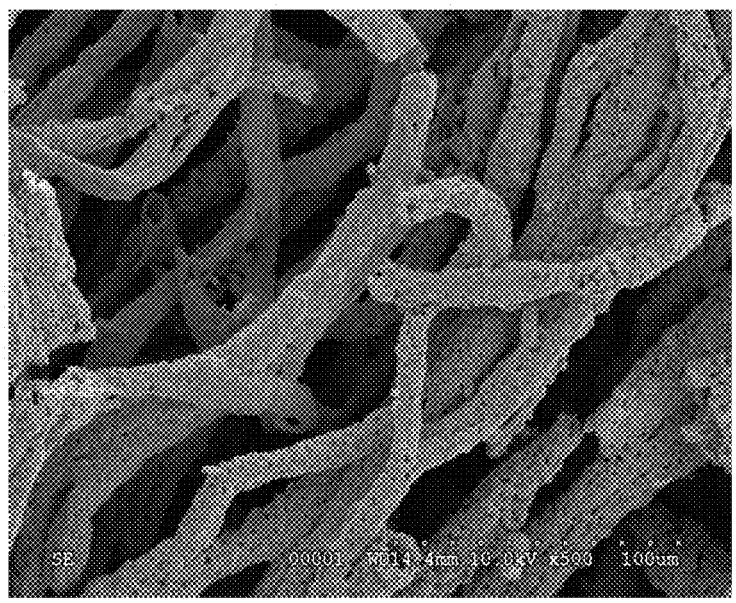
FIG. 8A depicts an SEM image of a Ag-Sponge.
Figure 8B:
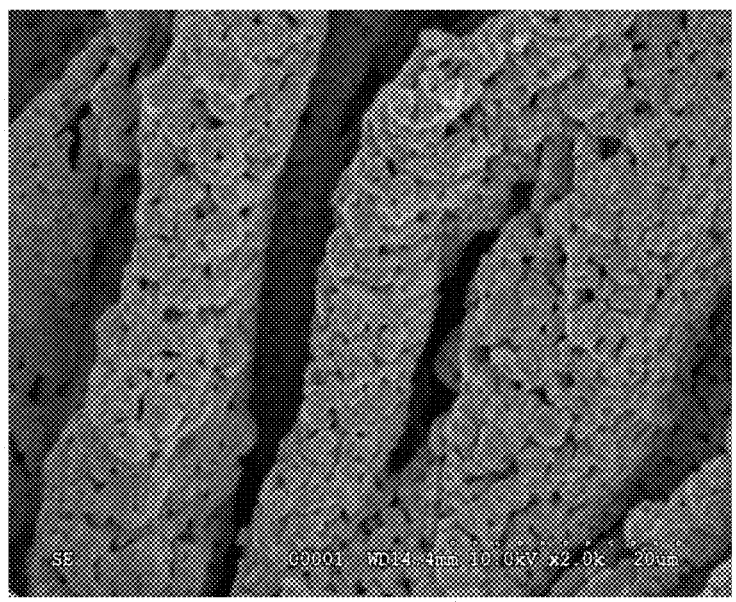
FIG. 8B depicts an SEM image of a Ag-Sponge at higher magnification.

FIGS. 7A, 7B, and 7C depict electron micrographs of Cu/C nano-metallic sponges at different magnifications; FIGS. 8A and 8B depict electron micrographs of Ag/C nano-metallic sponges at different magnifications. In both cases, note the tubular shapes, the high porosity walls, and the high surface areas. Nano-metallic sponges may be used in catalysis.

Example 1

The surface of the cellulose fiber is rough (FIG. 3A) and contains pores of diameter of 30-70 nm (FIG. 3B). These nanopores may allow reactant molecules to penetrate into inner cavities. When cellulose fibers were immersed in aqueous $CuSO_4$, copper ions were readily impregnated into the cellulose fibers through the pores. Though not wishing to be bound by this theory, most of the incorporated $Cu^{++}$ ions appeared to be bound to cellulose macromolecules, probably via electrostatic (e.g., ion-dipole) interactions, with the electron-rich oxygen atoms of polar hydroxyl and ether groups of cellulose.

Example 2

Cotton fiber was soaked in a copper sulfate solution. After the cotton was saturated, then extra solvent was removed. Carbonization was carried out at about 350° C. under nitrogen for about two hours. The copper nanoparticles and the encapsulating carbon shells appeared to have been formed simultaneously during carbonization. As fabricated, the CCCSNPs were uniformly distributed throughout the carbon based matrixes. FIGS. 1A, 1B, 1C, 1D, and 1F depict micrographs of fabricated copper-carbon core-shell nanoparticles made through the present invention. FIG. 1A depicts an SEM image that shows the carbonized cotton fiber (carbon black) with many nanoparticles located on its surface; FIG. 1F depicts a higher magnification of that depicted in FIG. 1A. FIG. 1B depicts a TEM image demonstrating that the nanoparticles formed through the entire carbonized cotton fiber; FIGS. 1C and 1D depict TEM micrographs of a nanoparticle encased in a carbon shell. These micrographs show a core of about 50-60 nm in diameter and a carbon shell of about 5 nm. FIG. 1E depicts an x-ray diffraction pattern for nanoparticle depicted in FIGS. 1C and 1D. This pattern confirms that the copper remained as $Cu^o$.

Example 3

The total copper concentration in the material made according to Example 2 was measured to be about 25 Wt %. It was clear from the TEM micrograph (See FIG. 1B) that the particles had generally spherical shapes, and that a majority of them appeared to have an average diameter value about 20-50 nm, although some particles were as small as one or two nanometers in diameter.

After the carbonized material was pulverized into micrometer to sub-micrometer sized particles, it was uniformly dispersed into both polar and non-polar solvent, for example water, aqueous acids, aqueous bases, salt solutions and cooking oil. After being immersed in water at ambient environment over three months, the nanoparticles still retained a reduced copper core structure with no sign of deterioration. The powder, characterized by FTIR, also showed that the shells of the CCCSN particles retained a number of organic functional groups. This property will be useful in functionalizing the carbon layer.

Example 4

Cotton fiber was soaked in a $AgNO_3$ solution. After the cotton was saturated, then extra solvent was removed. Carbonization was carried out at about 180° C. in nitrogen for about two hours. FIGS. 4A and 4B depict electron micrographs of the carbon-encased silver nanoparticles, at different magnifications.

Example 5

Cotton fiber was soaked in a NiSO$_4$ solution. After the cotton was saturated, then extra solvent was removed. Carbonization was carried out at about 380° C. in nitrogen for about two hours. The resulting nanoparticles contained carbon encased Ni, but the nanoparticles were difficult to distinguish with electron microscopy.

Example 6

Cotton fiber was soaked in a GdCl$_3$ solution. After the cotton was saturated, then extra solvent was removed. Carbonization was carried out at about 350° C. in nitrogen for about two hours. FIG. 6 depicts a micrograph of Gadolinium encased nanoparticles.

Example 7

The processes described in Examples 2, 4, and 6 were repeated using rayon fibers, wood fibers and cotton paper. All other reagents and conditions were the same. FIGS. 2A, 2B and 2C depict a micrograph of Cu in rayon.

Example 8

The process described in Examples 2, 4, and 6 have been used to make nanoparticles from a solution containing multiple metals, for example Cu and Ag. It appears that a Cu—Ag mixture was formed.

Using Copper Based Preservatives for Wood Protection

Example 9

The novel nanoparticles may be introduced into wood in the same general manner as other wood preservatives, e.g., pressure treatment. It is believed that this is the first report of using carbon-coated copper nanoparticles in the treatment of wood to protect against insects, mold, or decay.

There are several advantages to using CCCSNPs as wood preservatives. The cellulose source may be derived from bio-based renewable raw materials. Smaller amounts of Cu ions will be released in the environment due to the carbon encapsulation and lower metal loading. The material may be made at a competitive cost. The product is dispersible in both water and oil. The novel form of copper is compatible with existing wood treating processes in industry.

Example 10

Copper is toxic to marine life, particularly in the +1 or +2 oxidation state. One of the advantages of CCCSNP powder is that the encased copper will remain as metallic copper. We tested the stability of the CCCSNP by immersing the particles in a variety of solvents as listed in Table 1.

TABLE 1

Experimental design for chemical stability tests in designated solvents

| Solvent | Condition | No. of Tests |
|---|---|---|
| 1. water (pH = 7) and (pH = 2) | 1, 5, 10, 20, 30, 40, 50, 60, 90 days (t = 25° C. & 40° C.) | 36 |
| 2. 3% wt NaCl (pH = 7) and (pH = 2) | 1, 5, 10, 20, 30, 40, 50, 60, 90 days (t = 25° C. & 40° C.) | 36 |
| 3. Hexane | 1, 5, 10, 20, 30, 40, 50, 60, 90 days (t = 25° C. & 40° C.) | 18 |
| Total Number of tests | | 90 |

For all conditions tested (Table 1), we found that the copper remained stable as metallic copper, Cu°.

Example 11

A suspension of 1% CCCSNP in water was used to treat wood samples using a standard vacuum and pressure treatment, otherwise similar to that commonly used in wood treatment plants. The treated samples were subsequently challenged with Formosan subterranean termites (*Coptotermes formosanus* Shiraki) using the AWPA E1-jar test standard. The results showed that the novel materials greatly inhibited termite attacks on the treated samples.

Example 12

CCCSNP was combined with other biocides to form various preservative systems to deal with both copper-resistant and non-copper resistant fungi. Such co-biocides may include, for example, quat, tebuconazole ($C_{16}H_{22}ClN_3O$), RH287, and others known in the art. Tebuconazole and RH287 were formulated into emulsions to mix with the CCCSNP.

Example 13

Commercial #2 grade 2"x4" lumber from southern pine (*Pinus* spp.) and western spruce (*Pica* spp.) were cut into 48-inch long samples. The ends of each sample were coated with a commercial lumber sealer such as ANCHORSEAL® by U•C Coatings Corporation a "lumber end paint type" by Cloverdale Paint. The samples were pressure-treated based as shown below in Table 2.

TABLE 2

Experimental design on pressure-treatments with CCCSN solution

| Variable | Condition | Treatments |
|---|---|---|
| 1. Wood Species | Southern Pine and Western Spruce | 2 |
| 2. Treatment Pressure (PSI) | 120 and 160 | 2 |
| 3. CCCSN-Based systems | Quat, Azole, and RH287 | 3 |
| 4. Concentration (wt %) | 0 (control), 1, 2, and 5% | 4 |
| 5. Treating Process | 30-minute vacuum at 30-inch Hg and 60-minute pressurizing at target pressure level | 1 |
| Total Number of Treatments | | 48 |

A Twin-X x-ray preservative analyzer (Model 54-C-TX01—Oxford Instruments Analytical Ltd.) was used to analyze copper loading in CCCSNP powder and in treated lumber. For treated lumber, small thin wood slices, taken from various depths for each treated panel, were examined. The samples were ground into powder (40-mesh) and analyzed for copper. CCCSNP powder distribution and the copper penetration profile as the function of treatment conditions and wood morphology were determined by environment scanning electron microscopy (ESEM) with X-ray microanalysis. Micro-distribution of copper was also determined using scanning electron microscopy (SEM) with X-ray microanalysis. X-ray surface mapping and line scan provided the distribution surface elements as well as morphology information. X-ray image-chemical analyzer (EDAX) analysis showed copper within the wood; however, detail analysis will require higher Cu loadings in the wood. Micro-distribution of the copper within the wood, especially along the board thickness will be determined in the future.

Example 14

Leaching Tests

Figure 9:
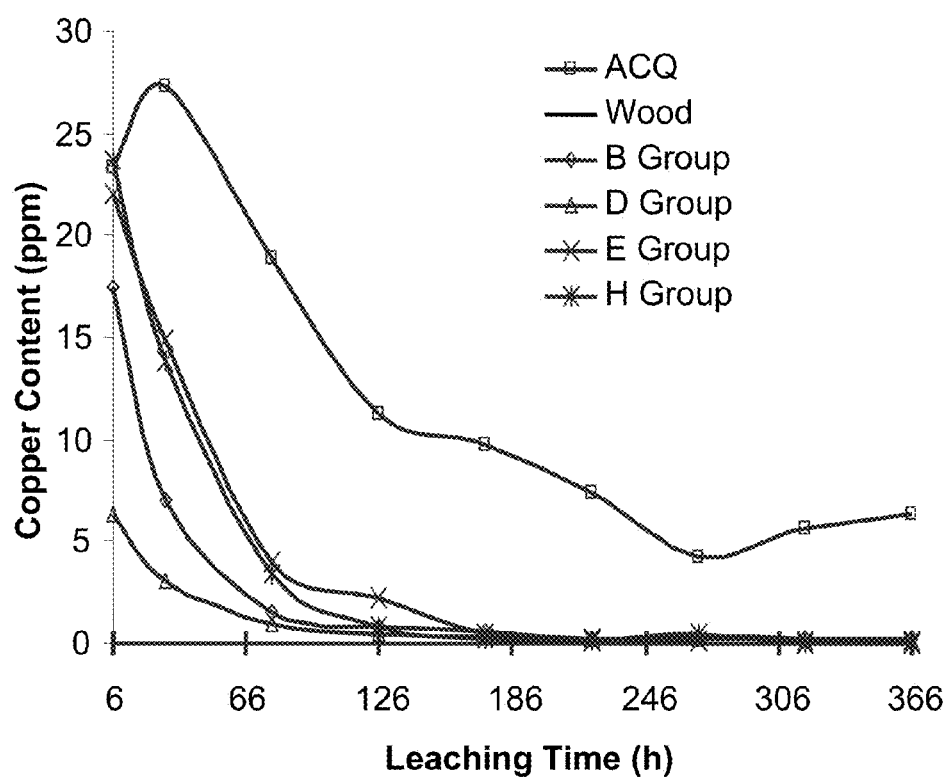
FIG. 9 depicts a graph of concentration of Cu in leachate vs. leaching time for leaching of Cu-core carbon-shell nanoparticles from wood.

Water leaching experiments were conducted according to AWPA leaching standard E11-97 [AWPA 2001c]. CCCSNP treated wood samples (19.0-mm cubes) were compared to Alkaline Copper Quaternary ("ACQ")-treated samples. The samples were subjected to AWPA leaching procedures over a total 14 day period. Leachate was removed at designated intervals. The total copper content in the leachate was analyzed as a function of time by Inductively Coupled Plasma Atomic Emission Spectrometry (ICP-AES). The method has a detection limit of about 0.1 mg/l, which is generally reproducible within ±8% for all analytes. The percent of copper leached is shown in Table 3 below and in FIG. 9. Group B, D, E, and H are described in Table 4. As can be seen the CCCS-NPs were retained in the wood substantially better than the standard copper formulation, ACQ.

TABLE 3

Copper concentration in the leachate as a function of leaching time measured ICP technique.

| | Copper Concentration (ppm) | | | | | |
| --- | --- | --- | --- | --- | --- | --- |
| Time (Hours) | ACQ | Control, Untreated Wood | B group | D- group | E- group | H- group |
| 6 | 23.28 | 0.016 | 17.51 | 6.37 | 22.00 | 23.72 |
| 30 | 27.34 | 0.005 | 7.02 | 3.06 | 14.94 | 13.79 |
| 78 | 18.91 | 0.011 | 1.52 | 0.92 | 3.99 | 3.42 |
| 126 | 11.23 | 0.006 | 0.79 | 0.45 | 2.28 | 0.79 |
| 174 | 9.77 | 0.003 | 0.59 | 0.37 | 0.48 | 0.27 |
| 222 | 7.38 | 0.003 | 0.27 | 0.22 | 0.19 | 0.14 |
| 270 | 4.22 | 0.01 | 0.31 | 0.19 | 0.16 | 0.42 |
| 318 | 5.67 | 0.00 | 0.24 | 0.12 | 0.11 | 0.04 |
| 366 | 6.31 | 0.01 | 0.22 | 0.11 | 0.10 | 0.06 |

Example 15

Termite Resistance Tests

Figure 10:
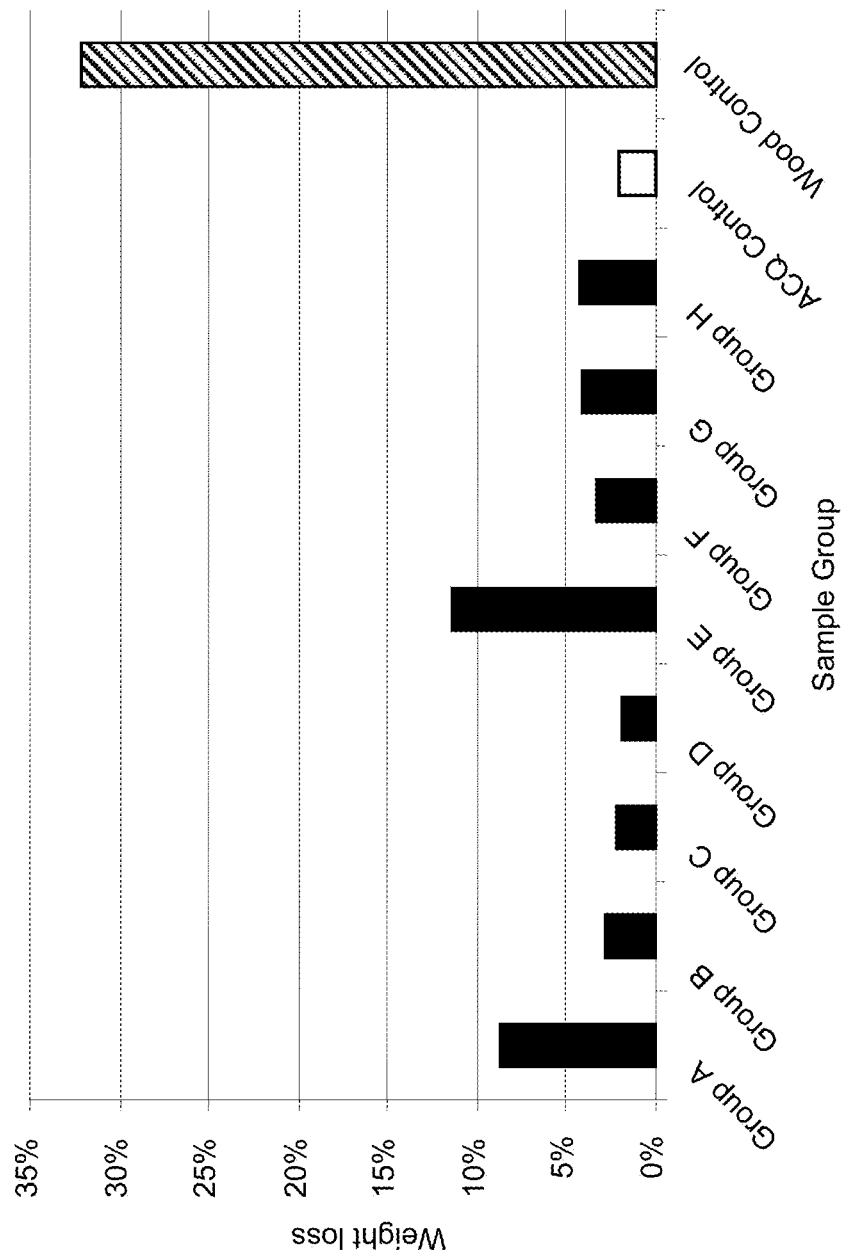
FIG. 10 depicts weight loss of wood due to termites as a function of treatment.
Figure 11:
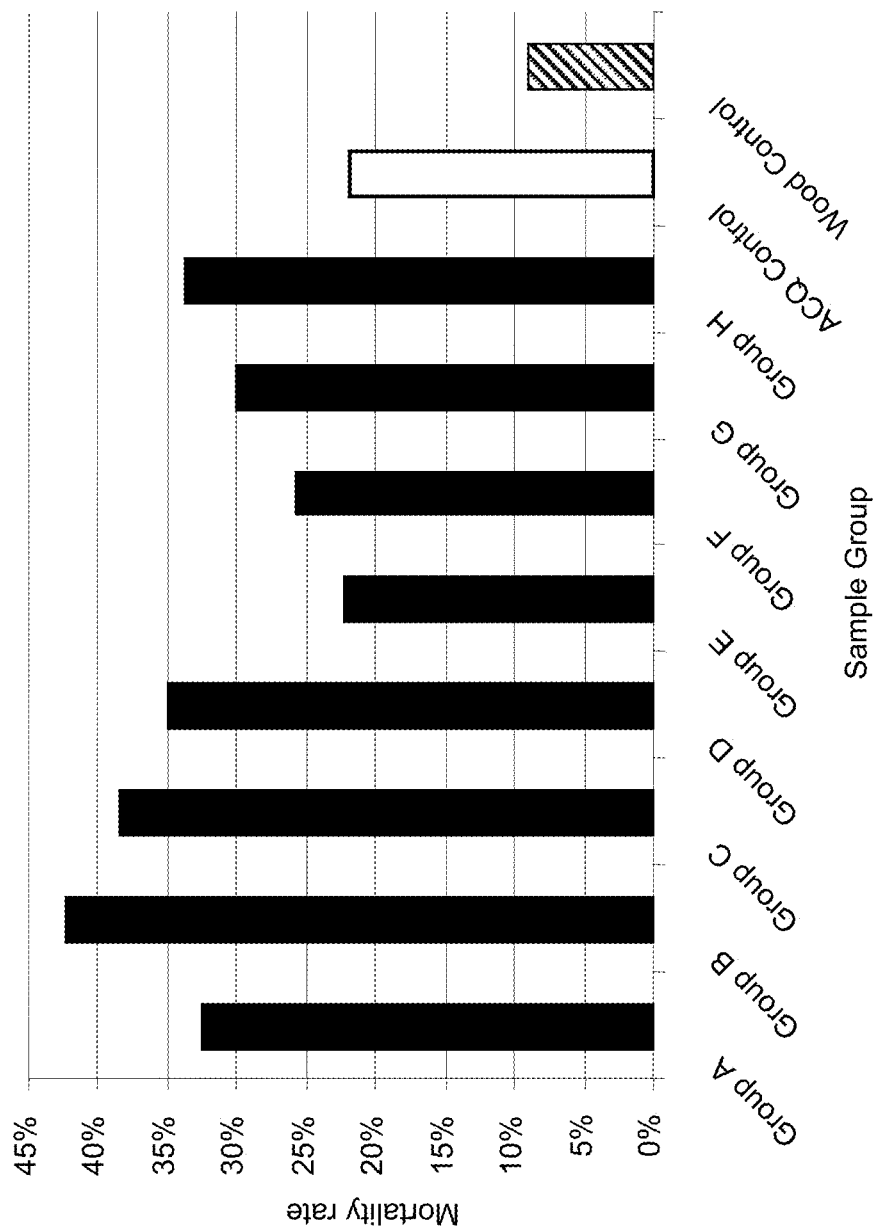
FIG. 11 depicts mortality of termites as a function of treatment.
Figure 12A:
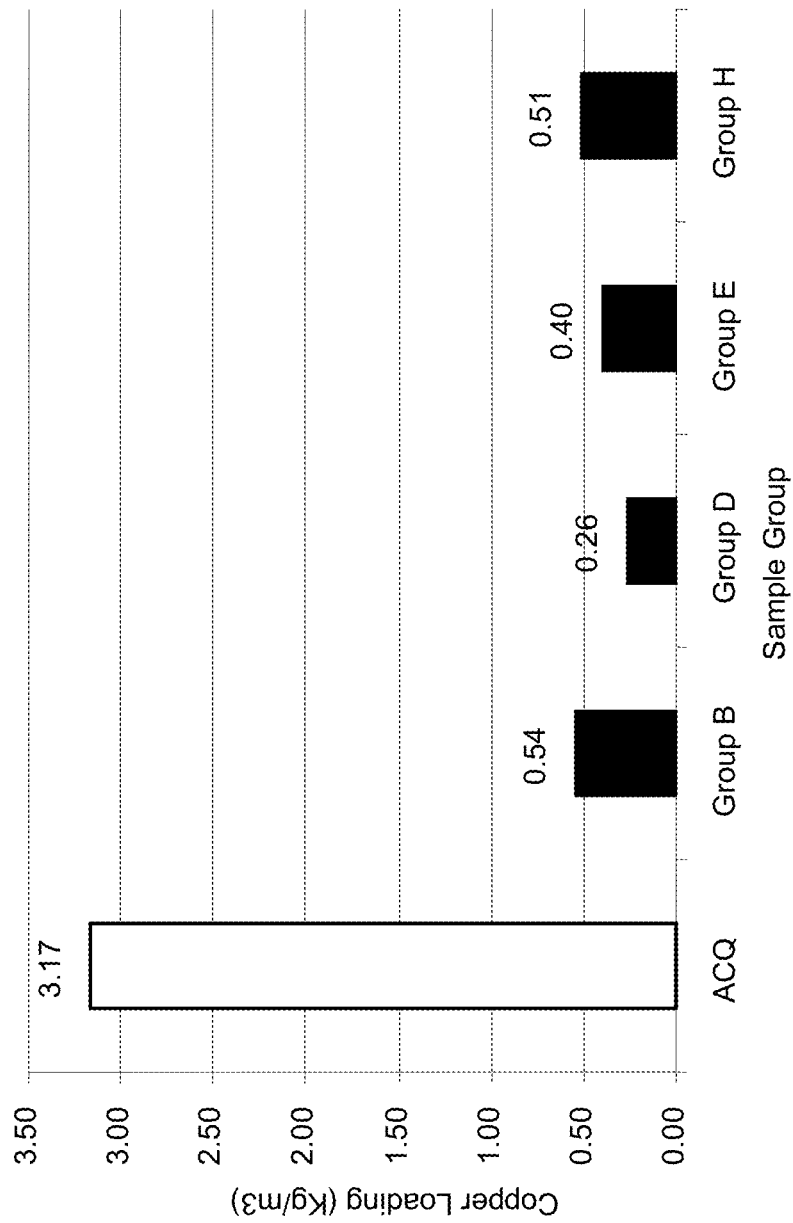
FIG. 12A depicts the loading of copper in samples tested for decay and leaching.
Figure 12B:
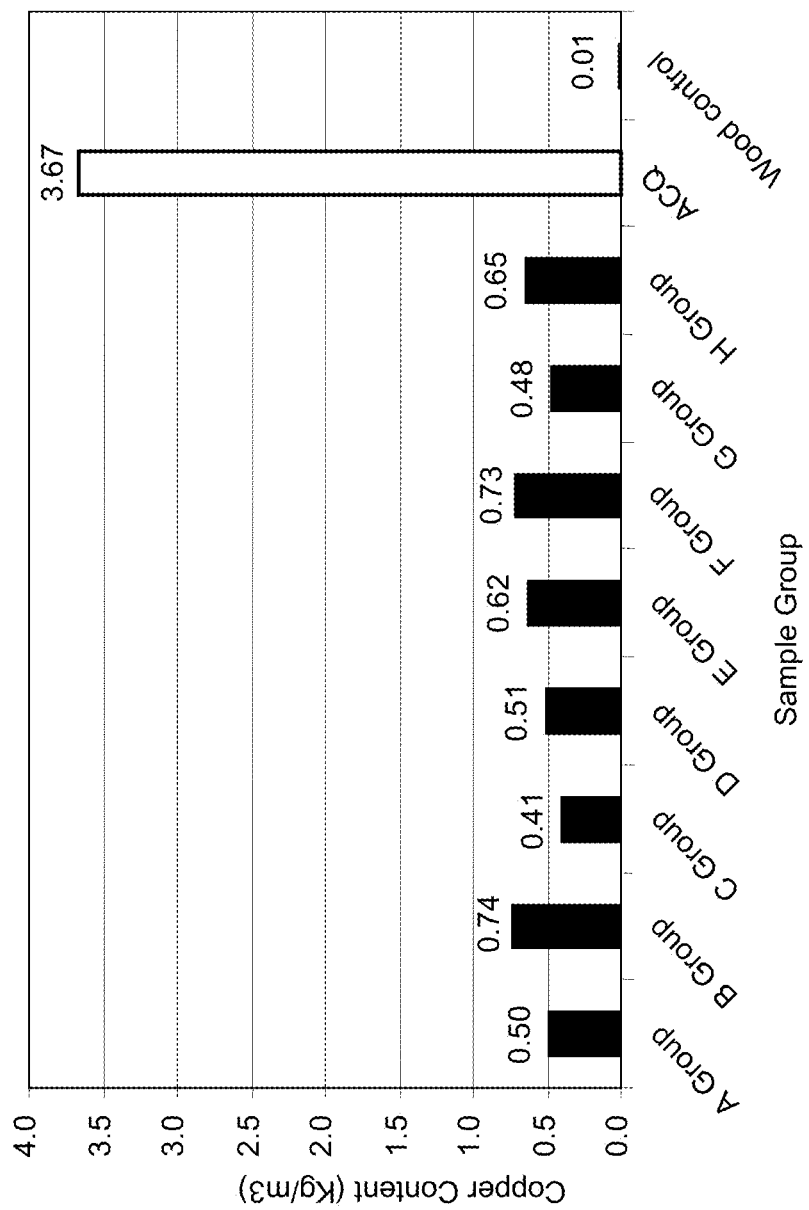
FIG. 12B depicts the loading of copper in samples tested for termites.

Five matched samples for each treatment condition, five ACQ treated samples and five untreated southern pine controls, were used in No-Choice Laboratory Termite Tests according to a modified AWPA standard E1-97 [AWPA 2001a]. FIG. 12B depicts the loadings of copper for the termite tests. Prior to each test, the blocks were oven-dried at 105° C. for 24 hours, and sample weight ($W_1$) and dimensions were measured. Each test bottle (80 mm diameter×100 mm height) was autoclaved for 30 minutes at 105 kPa and dried. Autoclaved sand (150 g) and distilled water (30 mL) were added to each bottle. Finally, four hundred termites (360 workers and 40 soldiers) were added to opposite sides of the test block in the container. All containers were maintained at room temperature for 4 weeks. The bottle cap was placed loosely. After testing, each bottle was dismantled. Live termites were counted, and test blocks were removed and cleaned. Each block was oven-dried again at 105° C. for 24 hours to determine the dry sample weight ($W_2$). From the measurements, sample weight loss [$(W_1-W_2)/W_1$] and termite mortalities were determined. The tested samples were ranked visually by five people on a scale of 1-10, with 10 as no damage and 1 as complete destruction. Table 4 below shows the results of this test. In the table both percent mortality and weight loss are given as well as a statistical ranking based on the Ducan protocol. Groups with different letters, for example A or B, indicate that the value in the table associated with one letter is statistically different from the value in the table associated with another letter. A group with two letters, for example CD, indicates the value in the table can not be distinguished from either of the groups with those letters. For example CD could not be distinguished from a group designated C or from a group designated D. By both weight loss and termite mortality it was clear that CCCSNP is effective against termites. FIG. 10 depicts the loss of wood as a function of treatment. FIG. 11 depicts termite mortality as a function of treatment.

TABLE 4

Summary of Termite Test Results

| Group | Copper loading rate (kg/m$^3$) | Mortality Rate (%) | | Sample Weight Loss (%) | | Damage Rating (0-10) | |
| --- | --- | --- | --- | --- | --- | --- | --- |
| Group A | 0.50 | 32.50% | BC | 8.75% | B | 6.5 | B |
| Group B | 0.74 | 42.30% | C | 2.80% | A | 8.3 | CD |
| Group C | 0.41 | 38.40% | BC | 2.25% | A | 8.4 | CD |
| Group D | 0.51 | 34.90% | BC | 1.90% | A | 8.8 | D |
| Group E | 0.62 | 22.20% | AB | 11.33% | B | 6.4 | B |
| Group F | 0.73 | 25.85% | BC | 3.35% | A | 8.3 | CD |
| Group G | 0.48 | 30.05% | BC | 4.07% | A | 7.8 | C |
| Group H | 0.65 | 33.71% | BC | 4.33% | A | 8.1 | CD |
| ACQ Control | 3.67 | 21.89% | AB | 2.05% | A | 9.9 | E |
| Wood Control | 0.01 | 9.04% | A | 32.09% | C | 1.0 | A |

Note that at a Cu loading for the ACQ control was about five to nine times the Cu loading for the Cu-core carbon-shell nanoparticles, while the effectiveness for termite control was about the same or better for the CCCSNP-impregnated wood at a far lower loading of copper.

Example 16

Flake Preparation

Commercial dry southern pine and mixed hardwood flakes were obtained. Part of the flakes were sprayed with an CCCSNP-based mixture (also including quat, tebuconazole, and RH287, based on solid wood tests) to achieve target copper loading levels around 0.25 and 0.45 wt %. The mixed flakes were used for making a composite wood product with incorporated CCCSNP.

Panel Manufacture

Experimental panels were manufactured using treated and control flakes according to the following conditions:

TABLE 5

Experimental design for strand board manufacturing with CCCSN-treated flakes.

| Variable | Condition | Treatments |
|---|---|---|
| 1. Wood Species | Southern Pine and mixed hardwoods | 2 |
| 2. Panel Density (g/cm$^3$) | 0.70 | 1 |
| 3. Copper loading | 0.25 wt %, 0.45 wt % | 2 |
| 4. Resin Content (%) | 4.5% of dry wood weight | 1 |
| 5. Panel Size | 24 × 24 × 0.5-inch | 1 |
| 6. Panel Structure | Single-layer random-formed | 1 |
| 7. Replication | Three each | 3 |
| Total Number of Treatments | | 12 |

The flakes and panels described above will be made. For each condition, the target amount of wood, resin, CCCSNP, and wax (used as a binder) will be weighed and mixed in a blender. Liquid resin and wax will be forced through two separate air-assisted nozzles, causing fine droplets to be sprayed into the blender with wood flakes. The CCCSNP powder will be added by a third air-assisted nozzle at about 40 PSI pressure. These conditions are similar to those used in a conventional process for loading zinc borate into wood. The blended wood flakes will then be removed and formed into mats. The mats will be hot-pressed into panels (1 minute closing and 5 minutes curing) using a 200-ton hot press. It is expected that such panels will be resistance to termites, mold and decay.

Example 17

As shown in Table 6, selected weights of CCCSNP were mixed with 1000 ml of water. Wood samples were placed in a 2000 ml plastic container, which were evacuated to about 27 mm-Hg for 30 minutes. The treating slurries were then introduced into the containers. The assembly, comprising wood and treating slurry, was then pressurized to 130 PSI (0.9 MPa) for about 60 minutes. After pressure was released, samples were removed, and then dried at about 80° C. to a constant weight. The treated samples were stored in plastic bags for subsequent testing.

TABLE 6

Formulation of the treating solution with 1000 ml water.

| Group | Amount of CCCSNP | Amount of Quaternary | Amount of EDTA |
|---|---|---|---|
| Group A | 10 g | 0 g | 0 g |
| Group B | 20 g | 0 g | 0 g |
| Group C | 10 g | 6 g | 0 g |
| Group D | 20 g | 6 g | 0 g |
| Group E | 20 g | 0 g | 15 g |
| Group F | 20 g | 6 g | 15 g |
| Group G | 10 g | 6 g | 0 g |
| Group H | Mixture of Groups A-G | | |

Example 18

CCCSNP-treated wood samples (19 mm cubes) prepared as described in Example 17 were tested for resistance to decay/leaching. These results were compared with commercial ACQ-treated wood samples of the same size. Three random samples were selected from each group. Samples were hammer-milled to 20-mesh. The powder was then digested in a sulfuric acid (42.5 ml)-water (200 ml) solution for three days. The digested solution was then filtered and diluted to 500 ml with water and analyzed for Cu content by Inductively Coupled Plasma Atomic Emission Spectrometry (ICP-AES). The copper concentration (kg/m$^3$) was calculated for each group based on measured sample volume and total copper content. FIG. 12A depicts the loading of copper for several of the samples.

Example 19

Figure 13:
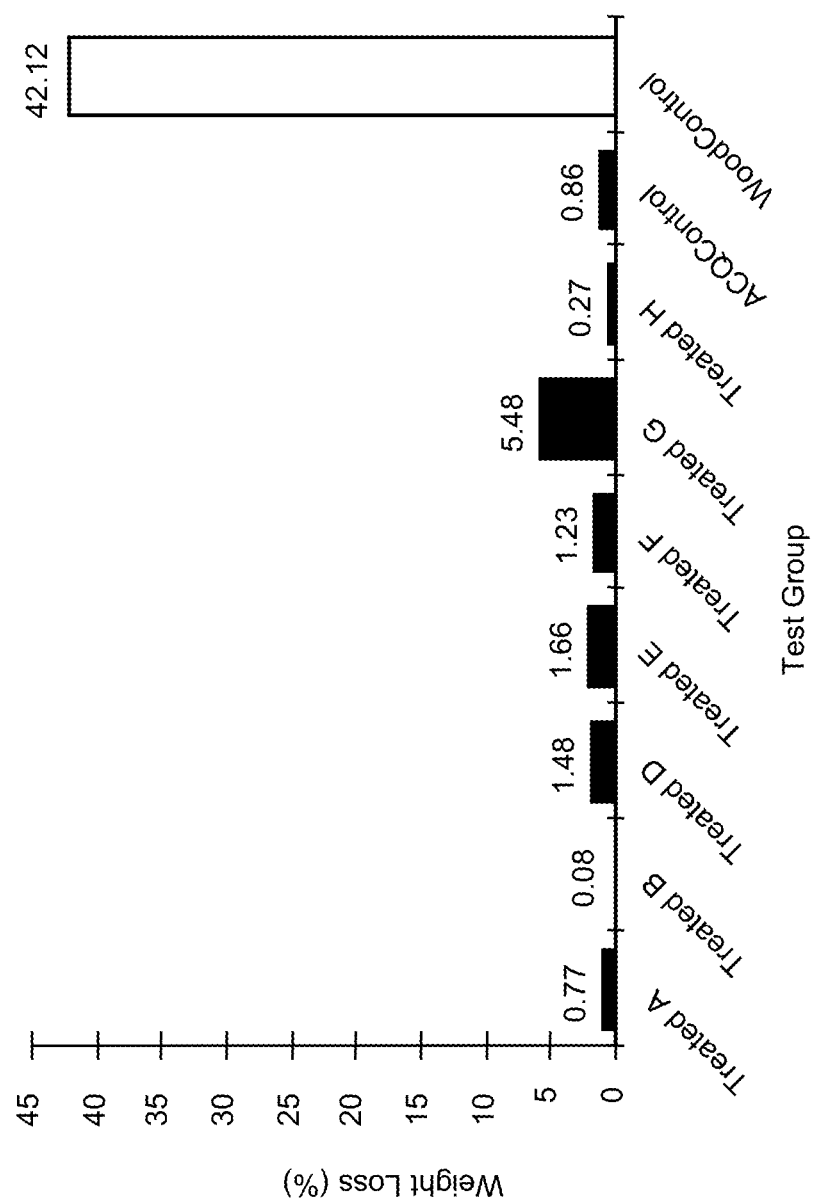
FIG. 13 depicts weight loss of wood due to *T. Vesicolor* (decay) as a function of treatment.
Figure 14:
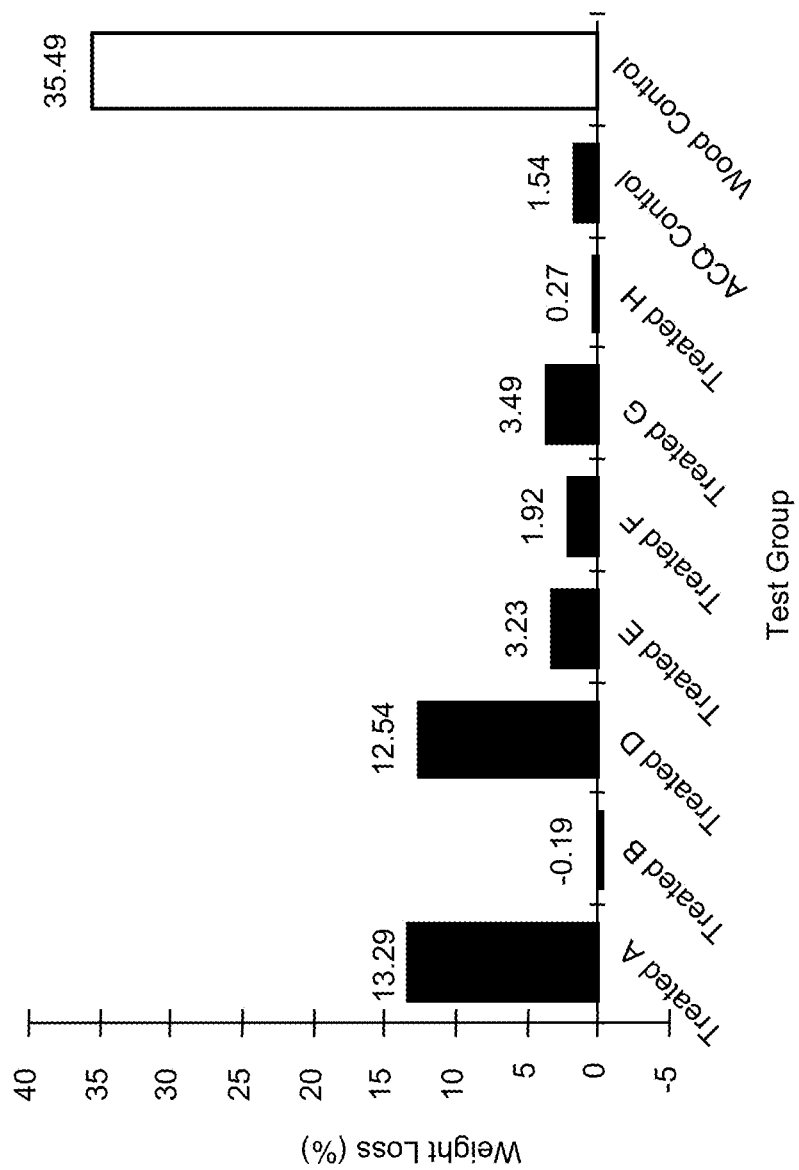
FIG. 14 depicts weight loss of wood due to *Irpex Lacteus* (decay) as a function of treatment.

The decay resistance of CCCSNP-treated wood samples was tested according to AWPA standard E10-01 [AWPA 2001b]. White fungi, *Trametes versicolar* or *Irpex Lacteus*, were used in the test. The culture media were sterilized at 105 kPa for 30 minutes at 105° C. and cooled before inoculation. 100 g of silt loam screened through a No. 6 sieve were placed in each bottle, which was loosely capped and autoclaved twice at 105 kPa for 30 minutes at 105° C. After the bottles cooled, untreated southern pine wood feeder strips were placed on top of the soil in each bottle. Each feeder strip was then inoculated at diagonally opposite corners. Each inoculated bottle was be incubated at 25° C. and 75% humidity until the feeder strip was heavily colonized by test fungus. The test blocks were then placed on the surface of a feeder strip colonized with fungus, one in each bottle. The testing time for both white rot fungi was 16 weeks. After the test, the test blocks were removed, cleaned, and oven-dried. Sample weight loss was calculated and analyzed. FIGS. 13 and 14 show the results of these tests. FIG. 13 depicts weight loss due to decay from *Trametes versicolar*. FIG. 14 depicts weight loss from decay due to *Irpex Lacteus*. Clearly the CCCSNPs are effective against these decays. Further, as can be seen from FIG. 12A, the copper loading for the AQC standard sample is 5-10 times that of the CCCSNPs. Thus, on a per weight basis the CCCSNPs are more effective than the commercial standard.

Example 20

Wood/Natural Fiber-Polymer Composites (WNFPC)

Melt-blending and compression molding methods were used to manufacture the Wood/Natural Fiber-Polymer Composites (WNFPC) with CCCSNP additive. During melt-blending, high density poly-ethylene ("HDPE") pellets were loaded into a Haake Rheomix 600 blender set at 165° C. and 60 RPM blender speed. After HDPE melting, CCCSNPs were added to the melt. In one embodiment wood fiber (40-mesh particle size) was added to the mix. In another embodiment bagasse fiber was added to the mix. A mixing period of 10 minutes was used to mix all components completely (i.e., the mixing torque reached stable conditions). The blend was cooled and removed from the blender.

The blends with various compositions were then used to make impact and tensile/dynamic mechanical analysis (DMA) test panels (4- and 1-mm thick, respectively) using compression molding. For each sample, the molding set was pressed at 175° C. and 30-ton compression force for 5 minutes, and then cooled to room temperature while maintaining the pressure. The target density was 1.0 g/cm$^3$. The test panels were conditioned prior to cutting of test samples. Test samples were machined and tested for tensile strength, impact strength, and dynamic modulus. See Table 7. These data show the ease with which the CCCSNPs may be included during fabrication of composites. Further, the composites containing CCCSNPs showed improved impact strength and tensile strength as compared to control composites, while dynamic modulus appears to be about the same as the control for most formulations tested. These composites are expected to be resistant against termites and decay just as impregnated wood was.

TABLE 7

Summary of test data on wood/natural fiber polymer composites

| Formulation Number | Composition | | | | Dynamic Modulus (MPa) | Tensile Strength (MPa) | Impact Strength (KJ/m$^2$) |
|---|---|---|---|---|---|---|---|
| | HDPE | Wood Fiber | Bagasse Fiber | CCCSNP | | | |
| 01 | 100% | 0% | 0% | 0% | 1543 | 27.37 | 3.96 |
| 02 | 98.5% | 0% | 0% | 1.5% | 1545 | 29.31 | 4.57 |
| 03 | 70.0% | 0% | 30% | 0% | 2348 | 23.22 | 3.74 |
| 04 | 68.5% | 0% | 30% | 1.5% | 2875 | 30.37 | 4.98 |
| 05 | 70.0% | 30% | 0% | 0% | 2474 | 19.97 | 3.02 |
| 06 | 68.5% | 30% | 0% | 1.5% | 2183 | 20.35 | 3.37 |

Example 21

Application to Trees

Figure 5A:
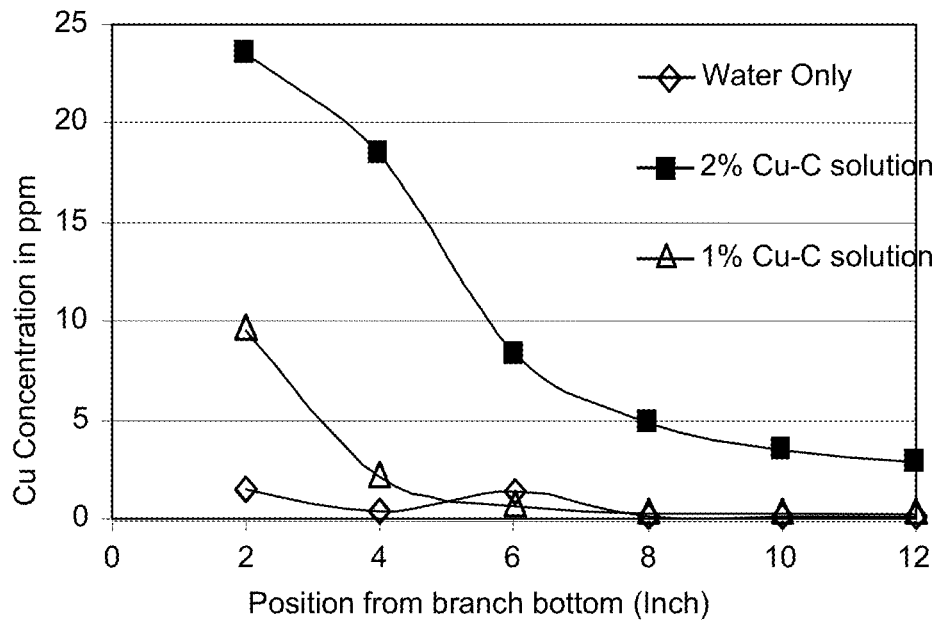
FIG. 5A depicts the amount of Cu-core carbon-shell nanoparticles taken into pine branches immersed in a slurry of Cu nanoparticles.

Four freshly cut pine branches, about 0.5 inches in diameter, were placed in glass tubes with one branch per tube. The tubes contained CCCSNP slurries at weight percents of 0.0%, 0.5%, 1%, and 2%. The branches were kept in these tubes for about 10 days, after which they were removed and sacrificed. The wood was examined with ICP. FIG. 5A depict the concentration of Cu in the tree branch as a function of distance from the bottom of the branch. Data from the branch inserted in the 2% slurry showed a concentration of about 25 ppm Cu at about 2 inches from the bottom. The Cu concentration decreased as a function of distance from the base, and was detected at about 5 ppm at about 12 inches from the base.

Example 22

Figure 5B:
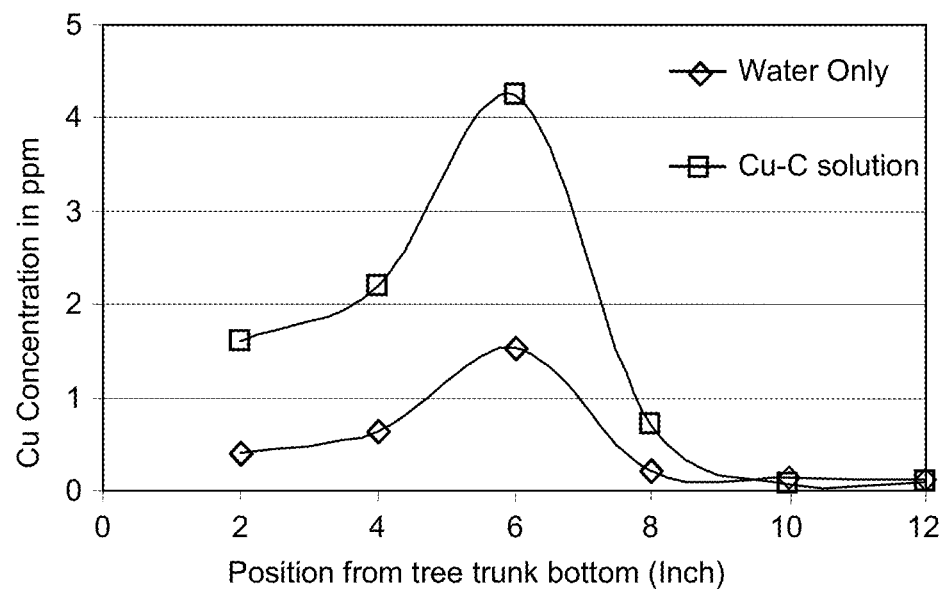
FIG. 5B depicts the amount of Cu-core carbon-shell nanoparticles taken into pine branches immersed in a slurry of Cu nanoparticles.

Two rose bushes were planted in standard nursery soil. One was watered with 1.5% slurry of CCCNSP, and the other bush was watered with pure water. After about three weeks we sacrificed the plants and determined the copper content as a function of distance from the trunk bottom using ICP. The first approximate 2 inch of the plant was in the soil. FIG. 5B depicts the concentration of Cu in the rose bush stem as a function of distance from the bottom of the plant. A peak in Cu concentration occurred at about 6" from the tree bottom. The concentration of Cu at its maximum was about 4.3 ppm.

Example 23

Different fibers (cotton, wood, bagasse, etc.) will be used to generate core-shell nanoparticles. As-harvested fibers will be compared to pre-treated (de-greased) fibers in terms of the resulting core-shell structure, particle size distribution, and particle density within the fiber, to determine whether the benefits of de-greasing justify the costs for use in the novel process.

Example 24

For some uses it will be useful to separate and collect the core-shell nanoparticles from the carbon matrix. For other uses, such as wood preservation, separation may not be necessary. In wood preservation, retaining the carbon matrix may actually be beneficial, both to better absorb other compounds that may also be helpful in wood protection, and also to help disperse the nanoparticles more uniformly through the wood structure. The "carbon matrix" comprises the black carbon residue compounds from the carbonized fibers. The "carbon shell" comprises the carbon layer(s) that are closely bonded to a metal nanoparticle core, typically with a thickness of a few nanometers. We have seen in TEM observations that the carbon shell on the copper nanoparticle surface has a different microstructure from carbon in the matrix. The FTIR results showed that there were substantial quantities of carbohydrate molecules in the carbon matrix but not in the shells. These differences may be exploited to separate core/shell nanoparticles from the matrix by chemical means, physical means, or both.

Separation methods include: (1) pulverizing the carbonized fibers with embedded nanoparticles to a fine powder, and screening the resulting powder from 100 µm to sub-µm to determine an optimal screen size for separation; in general, it is expected that finer powders and finer screens will yield better results, but may take more effort; (2) mixing the powder with an organic solvent such as acetone, so that the core/carbon shell nanoparticles start to separate from the carbon matrix, with stirring if needed. Preferably, the density and viscosity of the solvent are such that the carbon matrix with remain suspended, while the metal core nanoparticles will settle; (3) using ultrasonic, magnetic, centrifuge, or mechanical stirring will increase the separation speed and reduce the time needed for separation. Because acoustically cavitated bubbles produce high pressures, high pressure gradients, and fluid motion, this technique also may accelerate the separation processes; (4) separation may also be accomplished by applying a vacuum over a suspension containing a mixture of nanoparticles and carbon. Nanoparticles are expected to be pulled into the vacuum and collected directly with an air filter system. The carbon matrix phase will be examined by Energy Dispersive Spectroscopy (EDS) X-Ray Microanalysis and TEM to determine quantitative separation ratios and size effects on separation, respectively.

Example 25

Mold Tests

Mold testing will also be conducted following the testing procedures in AWPA "Standard Method of Evaluating the Resistance of Wood Product Surfaces to Mold Growth." Molds and their spores will include: *Aureobasidium pullulans* (d. By.) Arnaud ATCC 9348; *Aspergillus niger* v. Tiegh. ATCC 6275; *Penicillium citrinum* Thom ATCC 9849; and *Alternaria tenuissima* group (Kunze) Wiltshire Ftk 691B. The collected inocula will be dispersed in distilled water and distributed on potting soil in the mold chambers. The mold chambers will be left in warm humid conditions for more than two weeks prior to placing in the samples. The temperatures and humidity of the room will be periodically checked. The mold chamber will be kept at 25° C. and 100% humidity. Samples will be rated every 2 weeks for a total of 5 rating periods following the rating system in the AWPA proposed standard.

Definition: As used in the specification and claims, unless context clearly indicates otherwise, a "biological fiber" means a native plant fiber, a native animal fiber, a chemically- or physically-modified plant fiber, or a chemically- or physically-modified animal fiber. If the native fiber is chemically or physically modified, then its structure should retain sites that are effective as centers for promoting the formation of metallic core-carbon shell nanoparticles. The term "biological fiber" does not include synthetic fibers, regardless of composition or chemical or structural similarity, that are not derived from native plant fibers or native animal fibers. Examples of "biological fibers" include [please list as many specific examples as possible, from the existing specification or newly added, including particularly examples modified fibers]. Examples of fibers that are not considered "biological fibers" include the various synthetic nylons, polyesters, [add a few more examples, but the "excluded" list of examples need not be as long as the "included" list].

The complete disclosures of all references cited in this specification are hereby incorporated by reference. In the event of an otherwise irreconcilable conflict, however, the present specification shall control.

What is claimed:

1. A method for protecting wood, said method comprising impregnating the wood with metallic-core, carbon-shell particles, in an amount sufficient, in comparison to otherwise similar but untreated wood, to substantially inhibit the growth of mold in the wood, or to substantially inhibit fungal decay of the wood, or to substantially inhibit destruction of the wood by termites, or to substantially inhibit destruction of the wood by at least one wood-destroying insect species that is not a termite; wherein said particles comprise a metallic core and a carbon shell; wherein the diameter of said metallic core is about 10 µm or less; wherein said carbon shell completely encloses said metallic core, so that said metallic core has no exposed surface; wherein the thickness of said carbon shell is about 20 nm or less; wherein substantially all of said metallic core has a zero oxidation state; and wherein the metallic core is selected from the group consisting of aluminum, magnesium, copper, silver, zinc, and chromium.

2. A method as recited in claim 1, wherein the wood comprises a wood composite, lumber composite, wood fiber-polymer composite, laminated veneer lumber, parallel strand lumber, laminated strand lumber, particleboard, hardboard, medium density fiberboard, wood fiber-cement composite, hardwood lumber, or softwood lumber.

3. A method as recited in claim 1, additionally comprising impregnating the wood with a biocide other than the particles.

4. A method as recited in claim 1, wherein said impregnating comprises applying the particles to a living woody plant in an amount sufficient to cause the plant to take up the particles and to incorporate the particles in the plant's woody tissues in an amount sufficient to inhibit the growth of mold in wood produced from the plant, or to substantially inhibit fungal decay of wood produced from the plant, or to substantially inhibit destruction by termites of wood produced from the plant, or to substantially inhibit destruction of wood produced from the plant by at least one wood-destroying insect species that is not a termite.

5. A method for protecting a plant, said method comprising impregnating the plant with metallic-core, carbon-shell particles, in an amount sufficient, in comparison to an otherwise similar but untreated plant, to substantially inhibit the growth of mold in the plant, or to substantially inhibit fungal decay in the plant, or to substantially inhibit damage to the plant by insects; wherein said particles comprise a metallic core and a carbon shell; wherein the diameter of said metallic core is about 10 µm or less; wherein said carbon shell completely encloses said metallic core, so that said metallic core has no exposed surface; wherein the thickness of said carbon shell is about 20 nm or less; wherein substantially all of said metallic core has a zero oxidation state; and wherein the metallic core is selected from the group consisting of aluminum, magnesium, copper, silver, zinc, and chromium.

6. A composition of matter comprising wood impregnated with metallic-core, carbon-shell particles in an amount sufficient, in comparison to otherwise similar but untreated wood, to substantially inhibit the growth of mold in said wood, or to substantially inhibit fungal decay of said wood, or to substantially inhibit destruction of said wood by termites, or to substantially inhibit destruction of said wood by at least one wood-destroying insect species that is not a termite; wherein said particles comprise a metallic core and a carbon shell; wherein the diameter of said metallic core is about 10 µm or less; wherein said carbon shell completely encloses said metallic core, so that said metallic core has no exposed surface; wherein the thickness of said carbon shell is about 20 nm or less; wherein substantially all of said metallic core has a zero oxidation state; and wherein the metallic core is selected from the group consisting of aluminum, magnesium, copper, silver, zinc, and chromium.

7. A composition as recited in claim 6, wherein said wood comprises a wood composite, lumber composite, wood fiber-polymer composite, laminated veneer lumber, parallel strand lumber, laminated strand lumber, particleboard, hardboard, medium density fiberboard, wood fiber-cement composite, hardwood lumber, or softwood lumber.

8. A composition as recited in claim 6, wherein said metallic core comprises copper.

9. A composition as recited in claim 6, wherein said metallic core comprises zinc.

10. A composition as recited in claim 6, wherein said metallic core comprises chromium.

11. A composition as recited in claim 6, wherein said metallic core comprises silver.

12. A composition as recited in claim 6, additionally comprising a biocide other than said particles.

13. A living plant impregnated with metallic-core, carbon-shell particles, in an amount sufficient, in comparison to an otherwise similar but untreated plant, to substantially inhibit the growth of mold in said plant, or to substantially inhibit fungal decay in said plant, or to substantially inhibit damage to said plant by insects; wherein said particles comprise a metallic core and a carbon shell; wherein the diameter of said metallic core is about 10 µm or less; wherein said carbon shell completely encloses said metallic core, so that said metallic core has no exposed surface; wherein the thickness of said carbon shell is about 20 nm or less; wherein substantially all of said metallic core has a zero oxidation state; and wherein the metallic core is selected from the group consisting of aluminum, magnesium, copper, silver, zinc, and chromium.

14. A plant as recited in claim 13, wherein said metallic core comprises copper.

15. A fiber/polymer composite, impregnated with metallic-core, carbon-shell particles, in an amount sufficient, in comparison to an otherwise similar but unimpregnated fiber/polymer composite, to substantially strengthen said composite; wherein said particles comprise a metallic core and a carbon shell; wherein the diameter of said metallic core is about 10 µm or less; wherein said carbon shell completely encloses said metallic core, so that said metallic core has no exposed surface; wherein the thickness of said carbon shell is about 20 nm or less; wherein substantially all of said metallic core has a zero oxidation state; and wherein the metallic core is selected from the group consisting of aluminum, magnesium, copper, silver, zinc, and chromium.

16. A composite as recited in claim 15, wherein said composite comprises lumber composite, wood fiber-polymer composite, laminated veneer lumber, parallel strand lumber, laminated strand lumber, particleboard, hardboard, medium density fiberboard, and wood fiber-cement composite.

17. A composite as recited in claim 16, additionally comprising a biocide other than said particles.

18. A polymer impregnated with metallic-core, carbon-shell particles, in an amount sufficient, in comparison to an otherwise similar but unimpregnated polymer, to substantially strengthen the polymer; wherein said particles comprise a metallic core and a carbon shell; wherein the diameter of said metallic core is about 10 µm or less; wherein said carbon shell completely encloses said metallic core, so that said metallic core has no exposed surface; wherein the thickness of said carbon shell is about 20 nm or less; wherein substantially all of said metallic core has a zero oxidation state; and wherein the metallic core is selected from the group consisting of aluminum, magnesium, copper, silver, zinc, and chromium.

19. A polymer as recited in claim 18, wherein the polymer comprises polyethylene terephthalate, high density polyethylene, polyvinyl chloride, low density polyethylene, polypropylene, polystyrene, styrene acrylonitrile, acrylonitrile-butadiene-styrene, polycarbonate, nylon, or combinations of two or more of these polymers.

\* \* \* \* \*